US006639130B2

(12) United States Patent
Jang et al.

(10) Patent No.: US 6,639,130 B2
(45) Date of Patent: *Oct. 28, 2003

(54) PLANT STEROL REDUCTASES AND USES THEREOF

(75) Inventors: Jyan-Chyun Jang, Westerville, OH (US); Jen Sheen, Boston, MA (US)

(73) Assignee: The General Hospital Corporation, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/879,337

(22) Filed: Jun. 20, 1997

(65) Prior Publication Data

US 2003/0126630 A1 Jul. 3, 2003

Related U.S. Application Data

(60) Provisional application No. 60/022,086, filed on Jun. 21, 1996.

(51) Int. Cl.$^7$ .............................. A01H 5/00; A01H 5/10; C12N 15/29; C12N 15/82

(52) U.S. Cl. ...................... 800/306; 800/295; 800/298; 800/306; 435/69.1; 435/320.1; 435/410; 536/23.6

(58) Field of Search .............................. 435/69.1, 320.1, 435/419, 468, 410; 536/23.2, 23.6; 800/278, 286, 298, 295, 306

(56) References Cited

U.S. PATENT DOCUMENTS 5,512,472 A   4/1996  Lai et al.
5,759,801 A * 6/1998  Chenivesse et al. .......... 435/52

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*
De Block M. "The cell biology of plant transformation: Current state, problems, prospects and the implications for the plant breeding." Euphytica 71: 1–14, 1993.*
Gachotte et al., "An Arabidopsis mutant deficient in sterol biosynthesis: heterologous complementation by ERG 3 encoding a $\Delta^7$–sterol–C–5–desaturase from yeast", The Plant Journal, 8(3), 407–416 (1995).

Gachotte et al., "Isolation and characterization of an Arabidopsis thaliana cDNA encoding a $\Delta^7$–sterol–C–5–desaturase by functional complementation of a defective yeast mutant", The Plant Journal 9(3), 391–398 (1996).
Szekeres et al., "Brassinosteriods Rescue the Deficiency of CYP90, a Cytochrome P450, Controlling Cell Elongation and De–etiolation in Arabidopsis", Cell, 85: 171–182 (1996).
Li et al., "A Role for Brassinosteroids in Light–Dependent Development of Arabidopsis", Science, 272: 398–401 (1996).
Lecain et al., "Cloning by Metabolic Interference in Yeast and Enzymatic Characterization of Arabidopsis thaliana Serol $\Delta$7–Reductase", The Journal of Biological Chemistry, 271, No. 18, 10866–10873.
Kauschmann et al., "Genetic evidence for an essential role of brassinosteroids in plant development", The Plant Journal, 9: 701–713 (1996).
Corey et al., "Isolation of an Arabidopsis thaliana gene encoding cycloartenol synthase by functional expression in a yeast mutant lacking lanosterol synthase by the use of a chromatographic screen", Proc. Natl. Acad. Sci. USA, 90: 11628–11632 (1993).
Schaller et al., "Sterol overproduction is the biochemical basis of resistance to a triazole in calli from a tobacco mutant", Planta, 194: 295–305 (1994).
Zurek et al., "Investigation of Gene Expression, Growth Kinetics, and Wall Extensibility during Brassinosteroid–Regulated Stem Elongation", Plant Physiol., 104: 505–513 (1994).
Wang et al., "Brassinosteroid Stimulation of Hypocotyl Elongation and Wall Relaxation in Pakchoi (Brassica chinensis cv Lei–Choi)", Plant Physiol., 101: 965–968 (1993).
Schaller, et al., "Increased sterol biosynthesis in tobacco calli resistant to a triazole herbicide which inhibits demethylation of 14$\alpha$–methyl sterols", Planta, 187: 315–321 (1992).
Maillot–Vernier et al., "In Vitro Selection of Calli Resistant to a Triazole Cytochrome–P–450–Obtusifoliol–14–Demethylase Inhibitor from Protoplast of Nicotiana tabacum L. cv Xanthi", Plant Physiol., 93: 1190–1195 (1990).
P. Benveniste, "Sterol Biosynthesis", Ann. Rev. Plant Physiol, 37: 275–308 (1986).

(List continued on next page.)

Primary Examiner—Phuong T. Bui
Assistant Examiner—Russell Kallis
(74) Attorney, Agent, or Firm—Clark & Elbing LLP

(57) ABSTRACT

Disclosed are plant DNA molecules encoding C-14 sterol reductase polypeptides, as well as plant DNA molecules encoding polypeptides having at least 50% identity to the Arabidopsis C-14 sterol reductase; and vectors, cells and plants expressing such DNA. Also provided are methods for modifying the phenotype of a plant by expressing a C-14 sterol reductase DNA molecule in either sense or antisense orientations.

28 Claims, 29 Drawing Sheets

OTHER PUBLICATIONS

Lai et al., "The identification of a gene family in the *Saccharomyces cerevisiae* ergosterol biosynthesis pathway", Gene, 140: 41–49 (1994).

Lorenz et al., "Cloning, Sequencing, and Disruption of the Gene Encoding Sterol C–14 Reductase in *Saccharomyces cerevisiae*", *DNA and Cell Biology*, 11, 9: 685–692 (1992).

Russell et al., "Steroid 5α–Reductase: Two Genes/Two Enzymes", *Annu. Rev. Biochem.*, 63: 25–61 (1994).

Chory et al., "Phenotypic and Genetic Analysis of det2, a New Mutant That Affects Light–Regulated Seeding Development in Arabidopsis", *The Plant Cell*, 3, 445–459 (1991).

Schaller et al., "Expression of the Hevea brasiliensis (H.B.K.) Müll. Arg. 3–Hydroxy–3–Methylglutaryl–Coenzyme A Reductase 1 in Tobacco Results in Sterol Overproduction", *Plant Physiol.* 109: 761–770 (1995).

Taton, "Microsomal $\Delta^{8,14}$–sterol $\Delta^{14}$–reductase in higher plants", *Eur. J. Biochem.* 185:605–614 (1989).

Goad, "Application of sterol synthesis inhibitors to investigate the sterol requirements of protozoa and plants", *Biochem Soc. Trans.* 18:63–65 (1990).

Jang et al., "A critical role of sterols in embryonic patterning and meristem programming revealed by the fackel mutants or *Arabidopsis thaliana*," *Genes & Development* 14:1485–1497 (2000).

Schrick et al., "FACKEL is a sterol C–14 reductase required for organized cell division and expansion in Arabidopsis embryogenesis," *Genes & Development* 14:1471–1484 (2000).

\* cited by examiner

```
SEQ ID NO: 1   Ath    ..........  ..........  ..........  ..........  .....   0
SEQ ID NO: 4   Erg24  ..........  ..........  ......MVSA  LNPRTTEFEF  GGLIG  19
SEQ ID NO: 5   Pombe  ..........  ..........  .....MAKGA  VKKEKFEYEF  FGPIG  20
SEQ ID NO: 6   Sts1   ..........  MKSTVKKSAP  R.........  ........EF  GGAKG  18
SEQ ID NO: 7   Yg1022 MAKDNSEKLQ  VQGEEKKSKQ  PVNFLPQGKW  LKPNEIEYEE  GGTTG  45

Ath    ..........  ..........  ..........  .MLLDMDLGV  FLPSF  14
         Erg24  ALGISIGLEV  FTI....ILN  QMIRPDYFIK  GFFQNFDIVE  LWNGI  60
         Pombe  ALGVTVLTTV  VSFGSFYICN  EEGCPAKFSK  .ISHIFKKTP  LFDQ.  63
         Sts1   AIAIMTGFPC  LMY.YLWAGS  KFNDSQFIKP  ESFTIAGFQN  FFRTF  62
         Yg1022 VIGMLIGFFL  LMY.YMWIGA  EFYHGKVALP  K..AGESWMH  FIKHF  87

Ath    QSVYVLV...  ........F..  YFVYFAVAGE  ILPGKVIRGV  LFSF.  46
         Erg24  KPFRYYLGNR  ELWTVYCF..  WYGIFAVLDV  ILPGRVMKGV  QFRD.  102
         Pombe  KSFILYL...  ........F..  WFSTFTLLWK  CTNGKWAKGT  FIDD.  95
         Sts1   GHYIYVGAYP  TRYAFLVFWS  FCIVQAVMYL  TLPGVRTQGL  PLKHR  107
         Yg1022 YQFVLENGIP  EKYDWTIFLT  FWVFQIIFYY  TLPGIWTKGQ  PLSHL  132

Ath    .GSQFRYRCN  GL...LAFLF  LVAFLGICAK  LGIVSPLVVA  DRGLE  87
         Erg24  .GSRLSYKIN  GIAMSTTFVL  VLAIRWKFTD  GQLPELQYLY  FNHVS  146
         Pombe  KGTRFLYKIN  GFN.SACFFF  GVVCTSIYLL  GA.SCMEFIW  DNFLQ  138
         Sts1   NNERFFYLCN  AI...WSFYT  TIVFLAVFHV  THVFPITTFI  DMFGP  149
         Yg1022 KGKQFPYFCN  AM...WIFYV  TTTLVLVFHF  TNLFRLYVII  DRFGR  174

Ath    FFSATFIFCV  LVTLAFYVTG  ........RS  SSNKGSSF.K  PHVSG  123
         Erg24  ICIISILFSF  FLATYGFVAS  FIPLIFKKNG  NGKREKIFAL  GGNSG  191
         Pombe  FMFAFYVFBV  VLCTFCYVQS  FF........  .GKQQ..FAK  GGTSG  172
         Sts1   FMSVAFFTAF  VCTFVFYTGT  LLF.......  ..GDRLFDKP  HRLSG  185
         Yg1022 FMTCAFFSGF  AFSIFLYLWT  LFI.......  ..SHDY....  HRMTG  206

Ath    NLVHDWFFGI  QFNPQFMS.I  DLKFFF.VRA  GMMGWLLFNF  SILAK  166
         Erg24  NIIYDWEFGR  ELNPRLGP.F  DIKMFSELRP  GMLLWLLFNF  SCLHH  235
         Pombe  NILFDWFFGR  SLNPRLGN.F  DIKCFCEIRP  GLILWVVFDI  AFACH  216
         Sts1   NPIYDAFFGA  CLNPRLGKLF  DFKMFFEVRI  PWFILFFFSV  GAAVR  230
         Yg1022 NHIYDFFMGA  PLNPRWG.IL  DLKMFFEVRL  PWFTLYFFTF  GACLK  250

Ath    S..VQDGSLS  QSMIFYQIFC  AFYILDYFVH  EEYMTSFWDI  IAERF  209
         Erg24  HYLK.TGKIN  DALVLVNFLQ  GFYIFDGVLN  EEGVLTMMDI  TTDGF  279
         Pombe  QYLVLGGRIT  DSMVLVIIFF  TWYVLDSLIN  ESAVLFTMDI  TTDGF  261
         Sts1   QYETY.GTVS  PQVLFVCLGH  YFYANACSKG  EQLIVPTWDM  AYEKF  274
         Yg1022 QFETY.GYVT  PQLGVVMLAF  WFYANACAKG  EELIVPTWDM  AYEKF  294

Ath    GFMLVFGDLL  WFPFTFSFFQG  WFFLHNKV..  .EFTVPAIFV  NCLVF  251
         Erg24  GFMLAFGDLS  LVPFTYSLQA  RYFSVSPV..  .EFGWVKVFG  FLAIM  321
         Pombe  GYMLSFGDLV  WVPFLYSLQA  RYFAFIPV..  .DFGLVRTLA  FLCLQ  303
         Sts1   GFMLIFWNMA  GVPFTYSHCT  LYFFSFDPSV  YNWSTQYTTG  FYVLL  319
         Yg1022 GFMLIFWMIA  GVFFTYCHCT  LFFYYFDPSE  YHWSTLYNFS  LYVVL  339

Ath    FIGYMVFRGA  NKQKHIFKKN  PKTPI.....  ........WG  KFPVF  283
         Erg24  FLGFHIFHSA  NKQKSEFR..  ..QGF.....  ........FF  NLKFF  349
         Pombe  FLGYYIFRGA  NGOKNRFRSN  PNDPF.....  ........FK  HLKFF  335
         Sts1   FCCYFIFDTC  NGQKNFFRNQ  IYGTEVHRKT  FPQLPWLIIF  NPFTF  364
         Yg1022 FCAYYFFDTA  NAQKNAFRKQ  MSGDFFVRKT  FPFLPYQIFF  NPKYM  384

Ath    V...GGKFFV  SGFWGIARHC  NYFGDLMLAF  SFSFFPCGISS  FVFYF  325
         Erg24  QFKRGTKFFC  DGWWAKSQHI  NYFGDWFISF  SWGFATWFFT  FLAYY  394
         Pombe  QFKRGTKFFT  SGWWGMARHI  NYFGDWIMAW  AWCFPAGFGS  FIFYF  380
         Sts1   RCANGGTFFT  SGWFRYARKI  HYTADFFQSF  SWAFITGFQS  FLFFF  409
         Yg1022 VFSNGSYFFI  DGWFTLARKI  HYTADWTQSF  VWAFSCGFNS  VFPWF  429

Ath    YPIFFLFFFI  WRERFDEVRC  AEKYFEIWAF  YLRFVPWRIF  PYWF369
         Erg24  FSLFFATFFL  HRQQRDFHKC  RLKYGFFWFF  YERKVPYKIF  PYWF438
         Pombe  YVAYFGVFFV  HRNARDDHKC  RVKYGEDWFK  YCKAVKYRIF  PYWF424
         Sts1   YPSFFFVVLV  HRVSRDIKKC  KAKYGAFFDF  YCRIGPYLFI  PYFF453
         Yg1022 FPVFFLVVLI  HRAFRDQAKC  KRKYGFDWFE  YCKHGPYVFI  PYWF473
```

SEQ ID NO:2
```
        CTGAAATTAAACAAAGCGAGAAAAGGCGATACAAACGATTTCGAATGCTTCATCTTCTCC
      1 ---------+---------+---------+---------+---------+---------+  60
        GACTTTAATTTGTTTCGCTCTTTTCCGCTATGTTTGCTAAAGCTTACGAAGTAGAAGAGG
``` c

```
        TTTGAAAATCCTTCTTCTGCTTAATGCTGCTAGATATGGATCTCGGTGTTCTTCTTCCAT
     61 ---------+---------+---------+---------+---------+---------+  120
        AAACTTTTAGGAAGAAGACGAATTACGACGATCTATACCTAGAGCCACAAGAAGAAGGTA
``` c     SEQ ID NO: 1     M   L   L   D   M   D   L   G   V   L   L   P   S -

```
        CATTGCAATCTGTTTATGTGCTGGTGTTTTACTTCGTTTACTTGGCCGTTGCCGGAGAAA
    121 ---------+---------+---------+---------+---------+---------+  180
        GTAACGTTAGACAAATACACGACCACAAAATGAAGCAAATGAACCGGCAACGGCCTCTTT
``` c    L   Q   S   V   Y   V   L   V   F   Y   F   V   Y   L   A   V   A   G   E   I -

```
        TTCTCCCCGGGAAAGTTATTCGCGGCGTCCTTTTATCAGATGGCTCTCAACTTCGTTACC
    181 ---------+---------+---------+---------+---------+---------+  240
        AAGAGGGGCCCTTTCAATAAGCGCCGCAGGAAAATAGTCTACCGAGAGTTGAAGCAATGG
``` c    L   P   G   K   V   I   R   G   V   L   L   S   D   G   S   Q   L   R   Y   R -

Fig. 14-1

```
           GATGCAATGGTCTATTGGCACTAATATTGTTGGTAGCTATTTTGGGAATCTGTGCAAAAC
    241    ---------+---------+---------+---------+---------+---------+ 300
           CTACGTTACCAGATAACCGTGATTATAACAACCATCGATAAAACCCTTAGACACGTTTTG c         C  N  G  L  L  A  L  I  L  L  V  A  I  L  G  I  C  A  K  L -

TTGGCATTGTATCACCTCTTGTGGTTGCGGATAGAgGACTTGAgTTACTCTCAGCTACTT
    301    ---------+---------+---------+---------+---------+---------+ 360
           AACCGTAACATAGTGGAGAACACCAACGCCTATCTcCTGAACTcAATGAGAGTCGATGAA c         G  I  V  S  P  L  V  V  A  D  R  G  L  E  L  L  S  A  T  F -

TTATTTTCTGTGTTTTGGTGACATTAgCATTGTATGTTACTGGGCGAAGTtCCTCgAATA
    361    ---------+---------+---------+---------+---------+---------+ 420
           AATAAAAGACACAAAACCACTGTAATcGTAACATACAATGACCCGCTTCAaGGAGcTTAT c         I  F  C  V  L  V  T  L  A  L  Y  V  T  G  R  S  S  N  K -

AggGtTctTCCCTAAAgCCTCATGTCTCAgGAAATCTTGTACATGACTGGTGGTTTGGAA
    421    ---------+---------+---------+---------+---------+---------+ 480
           TccCaAgaAGGGATTTcGGAGTACAGAGTcCTTTAGAACATGTACTGACCACCAAACCTT c         G  S  S  L  K  P  H  V  S  G  N  L  V  H  D  W  F  G  I -
```

Fig. 14-2

```
       TACAGCTGAATCCTCAGTTTATGAGCATTGATCTCAAGTTTTTCTTTGTCAGAGCCGGGA
481    ---------+---------+---------+---------+---------+---------+ 540
       ATGTCGACTTAGGAGTCAAATACTCGTAACTAGAGTTCAAAAAGAAACAGTCTCGGCCCT c       Q  L  N  P  Q  F  M  S  I  D  L  K  F  F  F  V  R  A  G  M -

TGATGGGATGGCTGCTTATCAATCTCTCTATTCTGGCAAAAAGTGTGCAGGATGGTTCCT
541    ---------+---------+---------+---------+---------+---------+ 600
       ACTACCCTACCGACGAATAGTTAGAGAGATAAGACCGTTTTTCACACGTCCTACCAAGGA c       M  G  W  L  L  I  N  L  S  I  L  A  K  S  V  Q  D  G  S  L -

TGAGTCAGTCGATGATTCTTTACCAGATCTTCTGTGCGTTATATATATTGGACTACTTTG
601    ---------+---------+---------+---------+---------+---------+ 660
       ACTCAGTCAGCTACTAAGAAATGGTCTAGAAGACACGCAATATATATAACCTGATGAAAC c       S  Q  S  M  I  L  Y  Q  I  F  C  A  L  Y  I  L  D  Y  F  V -

TTCATGAAgAATACATGACCTCTACGTGGGACATAATTGCAGAGAGACTAgGCTTCATGC
661    ---------+---------+---------+---------+---------+---------+ 720
       AAGTACTTcTTATGTACTGGAGATGCACCCTGTATTAACGTCTCTCTGATcCGAAGTACG c       H  E  E  Y  M  T  S  T  W  D  I  I  A  E  R  L  G  F  M  L -
```

Fig. 14-3

```
         TAGTGTTTGGAGATCTCCTGTGGATTCCTTTCACTTTTAGCATTCAGGGCTGGTGGCTTT
     721 ---------+---------+---------+---------+---------+---------+ 780
         ATCACAAACCTCTAGAGGACACCTAAGGAAAGTGAAAATCGTAAGTCCCGACCACCGAAA c      V  F  G  D  L  L  W  I  P  F  T  F  S  I  Q  G  W  W  L  L -

TGCACAACAAAGTAgAACTAACAGTTCCTGCGATTGTAGTCAATTGCCTTGTCTTCTTGA
     781 ---------+---------+---------+---------+---------+---------+ 840
         ACGTGTTGTTTCATcTTGATTGTCAAGGACGCTAACATCAGTTAACGGAACAGAAGAACT c      H  N  K  V  E  L  T  V  P  A  I  V  V  N  C  L  V  F  L  I -

TAGGGTACATGGTTTTTCGAgGAgCTAACAAACAAAAACATATCTTTAAGAAGAACCCAA
     841 ---------+---------+---------+---------+---------+---------+ 900
         ATCCCATGTACCAAAAAGCTcCTcGATTGTTTGTTTTTGTATAGAAATTCTTCTTGGGTT c      G  Y  M  V  F  R  G  A  N  K  Q  K  H  I  F  K  K  N  P  K -

AAACACCAATATGGGGCAAGCCTCCAGTGGTAGTTGGTGGAAAGTTACTGGTTTCAGGCT
     901 ---------+---------+---------+---------+---------+---------+ 960
         TTTGTGGTTATACCCCGTTCGGAGGTCACCATCAACCACCTTTCAATGACCAAAGTCCGA c      T  P  I  W  G  K  P  P  V  V  G  G  K  L  L  V  S  G  Y -
```

Fig. 14-4

```
        ATTGGGGAATTGCAAGGCACTGTAATTACCTTGGCGACTTGATGCTTGCTCTGTCCTTCA
 961    ------------------------------------------------------------  1020
        TAACCCCTTAACGTTCCGTGACATTAATGGAACCGCTGAACTACGAACGAGACAGGAAGT c      W  G  I  A  R  H  C  N  Y  L  G  D  L  M  L  A  L  S  F  S -

GTTTGCCATGTGGAATAAGTTCTCCGGTTCCATATTTCTACCCGATATACCTTCTGATAC
 1021   ------------------------------------------------------------  1080
        CAAACGGTACACCTTATTCAAGAGGCCAAGGTATAAAGATGGGCTATATGGAAGACTATG c      L  P  C  G  I  S  S  P  V  P  Y  F  Y  P  I  Y  L  L  I  L -

TATTGATATGGAGAGAACGAAGAGACGAGGTTCGATGTGCAGAGAAGTACAAGGAGATAT
 1081   ------------------------------------------------------------  1140
        ATAACTATACCTCTCTTGCTTCTCTGCTCCAAGCTACACGTCTCTTCATGTTCCTCTATA c      L  I  W  R  E  R  R  D  E  V  R  C  A  E  K  Y  K  E  I  W -

GGGCAGAGTATCTTAGACTTGTCCCCTGGAGAATACTTCCTTATGTTTATTAGATGTGCC
 1141   ------------------------------------------------------------  1200
        CCCGTCTCATAGAATCTGAACAGGGGACCTCTTATGAAGGAATACAAATAATCTACACGG c      A  E  Y  L  R  L  V  P  W  R  I  L  P  Y  V  Y  *
```

Fig. 14-5

```
                AAGAGCCAAGTCATGAAtCCTTTCAGATTCACCTCTTGTTGTCTTATTTTTTCCATAATC
       1201    ---------+---------+---------+---------+---------+---------+  1260
                TTCTCGGTTCAGTACTTaGGAAAGTCTAAGTGGAGAACAACAGAATAAAAAAGGTATTAG c

TTGTTTTATTTTAGCAATGCTCGAATTGAAACTTTGTAGTACACTTTTGAAAAATAACTT
       1261    ---------+---------+---------+---------+---------+---------+  1320
                AACAAAATAAAATCGTTACGAGCTTAACTTTGAAACATCATGTGAAAACTTTTTATTGAA c

CAGTCCTTAAAAAAAAAAAAAAACCTAANTTACTCCCNCTGGGCGGCCGCTGGTTTTATAT
       1321    ---------+---------+---------+---------+---------+---------+  1380
                GTCAGGAATTTTTTTTTTTTTTTGGATTNAATGAGGGNGACCCGCCGGCGACCAAAATATA c

TTGTTGTAAAAATTAAANAATTACTNCCTTGANGATCTGTAAAAAAAAA
       1381    ---------+---------+---------+---------+---------   1429
                AACAACATTTTTAATTTNTTAATGANGGAACTNCTAGACATTTTTTTTT
```

Fig. 14-6

SEQ ID NO: 3

```
   1 TNTTGAAGGN TNAAGAAAAA NTANGGTAAG CTGGGNAGGA CAAGANTTCT
  51 TGTNACCACA ACACAACAAC GCCATGAACC NATCGGTTTC TTNTGTTTNG
 101 AGATCACCTT TCTTGAGTTG GTGGTTTCTG AGNTCAAGNT CCTTGTTGAC
 151 TCAGTGAAGT CCAGATGCAG CNTCAAAACT TTTGTCCTGT AGACNTAGCA
 201 AGAGTAACAG CACCAACCAA ATCGCTATCC GATGTAATCA AAACCTTATC
 251 ACNTTCATCG TCCTCATATA TAATCTGAGG CCGTTGTTCC ACATTGTTAT
 301 TGTCGCTGCC AATTCTTTGC ATCACAATAC CCATCAGCTN TTCGAGGTTT
 351 TCAGCTCCAG AAGTAAACCG ATGTACACGG CCCTTAAGGT CTTCAAATTT
 401 GAACGAAAAC GAATTCCCTA GTCCTAGAGA TGGGTAAGAA CTGAGCTTCC
 451 CTATATCTGA ATGATGCATC ATTGCCGACA TTTCACTTTG AGTGTCAGAA
 501 TCATCAGGTG GCTCTAACGC AAGAGCTGAA TCCCAAAATT TCTGCATCAT
 551 CGTGTTTGCC ATATCATTTA CAGCTCCAGA ACTGTTCTCC ACCATTGAAA
 601 TAGCTGCGTG AGTAATCTGA AGAACGTCTA CACAAGCTGC AGCTGATCCA
 651 TCTTTATCTA TAATTGGAAG ATGTAGAAAC TTTCCATCAT GCATTGTATG
 701 CAATGCATCC AGAATCGTTG TCTCTAGCGA TGCACATTCA GGATTCGGTG
 751 TCATTACCTT CTCGACAAGA GTCAATTCAG GAGATAAATT TTGTGCCACC
 801 ACTCGCATCA GAATGTCCTT TGAAGTCAAG ATTCCACTGA TTTTGTTCCC
 851 CCGTGGAAAT GATTACAGAG TTAACCCGCA AATCCCTCAT CCTTTTCGCA
 901 GCAACTGAAA CAGGATCTGA TGGTGCTACA AGTGCAACCT TCGATGTCTG
 951 TAATAATCGT GACAAGGCGG GTTAAACATT NTNTCCTTCA AGGTTTCAAT
1001 GAAAGCATAC GGTGCAGAAT ATCCGCTTCC CCATTGTTTN TCCACACCTT
1051 CCACTGCAGC AGCTAAAGCA CTACCTTGCT CTGCAGTTTC TCCATCCTAG
1101 AAATAGCATC ATACAAACAC TTTGTAATAT CCAACAAAGC AATGACTTCA
1151 CCATTCTCCA CAACAGGCAA GTGTCTAAAC TTCCCTTGAA CCATCTTCTG
1201 AAGAGCCTCA AGCGCCAACG AATCAGAAGT AACAAAAATA GGATTCCTAG
1251 TCATAACCTT AGAGACCAAA GTTTGATCCG GTCTCAACCC TTCAGCAATC
1301 ACTCTTGTAG CTACATCTTT ATCAGTAACA ATCCCGGAAA GAAGCGCACT
```

Fig. 15-1

```
                    SEQ ID NO: 3
1351  TGAATCAGTC  AACAAACAAG  CATCAACACG  CCTAGCAGCC  ATTNTTCGAC
1401  AAGCATCGAA  AACAGTAGTT  CCTTCNAGGA  ATAGTAAGAG  CTTTCGATAA
1451  CCTAAGCTTC  TTCGCTGTCT  CTCTCCATTA  GAAGGAGCTT  GAGATTGAGG
1501  TTGAGGAGGA  GGTGAATTGG  GTTTTGAGGT  GTTCCCANTA  ACACTTCCAT
1551  TCTCTGATTG  TACTGGTTTC  TTAGAAGGTG  GTGGTCCTCN  CCGTACAGTA
1601  GAATTGCTTC  TCCTCCCTGA  TGTTGAAGAA  GGACCCGTCG  CTTGAGTACT
1651  CATATTCGGT  CAATCTAGGG  TTTACTTAGA  TCCTAAATCC  GTCANAAATG
1701  ATTCCTTTAG  ATATCAAACT  CGTCTCTGCA  AATGAAAAAT  TCAACCTTTA
1751  ATTCACAAAC  TATTGAAATT  TCATCTAAAG  CACGAATCTG  AATAAAACCC
1801  AATTCACAAT  AAAGACGATT  TGCTCTGAGA  ATACGATGCA  ACATACACGA
1851  AAAGGATTCG  AATTTAACGG  ACGAGGGAAA  TGAAACAACT  TGAAACCCTA
1901  AGGATTTGAG  CAGAAGTTAT  GTGGGAAGAT  TGGGNATTTA  GGGTTTACCT
1951  TCTTCTTTCT  TCNTCAAGGT  CTCTCTCTCG  AGCACTTTCG  TTNCCCCAAA
2001  AACNAACGGC  TCTTAACAAT  TGAGTTAANC  CANTTATCGA  GTTTTCATTG
2051  GNTGTTCCTG  TTTCCGCGTG  TGTGGTGGNT  CNCCACCTCC  TTTCTTATAA
2101  TCNACGACTA  AAAATGTTAA  ANATAANACT  AANATTTCTT  TCTANAAAAA
2151  TCGTAAAANC  CAAATGTTTT  TTTTTTTCTG  ATAAATGTCT  ATAAATCACC
2201  CTTTCTTTTT  AAATAATGAA  ATTTGATGAC  ATTTATCTCT  TGTATCTAGN
2251  AGAGTTAATG  GCTAACATAA  ANACCAAAAA  AAATTAATTC  NAATAAATAT
2301  GATTTGTGTG  GGTTACATGG  AAAAATTGTC  AAATAATAAA  NCAAAAAAAA
2351  ATTGTATAGA  TGCAGTGCAA  GTTGTTTCTG  GTCAACTTGC  CGTCGAGCCT
2401  CACAACTGTT  TGTTACAAGT  GGACTCGCAT  GTAATTCCCT  CTTTTAATAA
2451  CTTACCAGTT  ACACCATCCA  ACATGTGATT  TGACAGAAAA  ATATTTTAGT
2501  GAAATGTGAT  CGGTGCAGAT  TTTTCTATGT  ACGTTTAAGC  CTTTAAGGTA
2551  GACGTTTAAT  CCNAAAATAT  CCCTGAATAA  CAACACCGAT  TAATGGAACC
2601  AAGTAGATAC  CTCCTCCGTT  TGGATGGCTC  AAATGCAACC  ATGATGCAAG
2651  CTTTTGCGAT  TGACCCAAAG  TGAGAGAACT  AGATCGAGAT  GGATTATTCG
```

Fig. 15-2

```
                       SEQ ID NO: 3
2701   GAACCATTAC CGCACCCTTA TATAATGGCA GCATCTTAAT AGTAAACAAA
2751   AGCTTTAGCC TTAGGTTTTA GCTTCCTTCA CTCTTTGCAT ACATTGTGAA
2801   TCTGCGGTTT TAGATGGACC ATAGTGGAAA AAGGCTTTCA TCAATAACTC
2851   GTGGACTTGA TCAATGGTAG AAAAGANAAT ACATAGTATG GAAAACTAGA
2901   TATTTGATAT ATTTGGTTCA AACTCTTATC CGGTGTTGAG GTGATATACA
2951   CATGAAGACA TAACAATCGC ATAGCCGAGA AACTAGTATT CATTAACCTT
3001   TTTCTCTAAA GAGATTGTCC TATCAATCTA AATTTTAGAT GTTAAAAAAA
3051   AAATggtaag gttaaacagg ccgctaggtt ggttttacga tgatgtaaaa
3101   agtagccatc ttaaaataac agtcgtttgc gagactggcc aggccatccc
3151   atgggccata ggctcgctca agttgTGCTT GGCAGAATTT AGTAACTTGG
3201   GGTTTTGTTA TCAACAATCA ATAGTTTAAG GCTTTACCTG CAAGAAATGA
3251   AGAGTTTAAG GGTTCTTTTT GGTATTCCCG ATTCACACAA GTGAGCTAGC
3301   TCATCAGAGT CCACGAGCTT CCCACTAAAA AATTGAAAAT TGTTGCTTCT
                       ┌──────→ ELL
3351   GTCATCTGAA ATTAAACAAA GCGAGAAAAG GCGATACAAA CGATTTCGAA
3401   TGCTTCATCT TCTCCTTTGA AAATCCTTCT TCTGCTTAAT GCTGCTAGAT
3451   ATGGATCTCG GTGTTCTTCT TCCATCATTG CAATCTGTGA GCTGTCTCTT
3501   TAGCTTTTGA CTGTTGCAAT TGTTATTGTG AAATTTTTGT TCGCTTTTGG
3551   ATCAGCTTTT GTTAAATTCG TTCGAGATT TTAGGTTTAT GTGCTGGTGT
3601   TTTACTTCGT TTACTTGGGN CGNTGGCGGA GAAATTCTCC CCGGGAAAGT
3651   TATTCGCGGC GTCCTTTTAT CAGATGGCTC TCAACTTCGT TACCGATGCA
3701   ATGGTATATT TGATTTGATT TACTCTCTCT ACAATTCCTG AGAGTCTGTG
3751   AGCTCGAAAG TTCATTTCCA TTAGTTTGGT TAATTCAATT TCAGGTCTAT
3801   TGGCACTAAT ATTGTTGGTA GCTATTTNGG GAATCTGTGC AAAACTTGGC
3851   ATTGTATCAC CTCTTGTAAG TGTAGTTACA AGATTTCGAT TGTATTTCTA
3901   TGAATCCGAA TGCTATATGC TATATGAATC CGATTGCAAT TGCTTTCTCA
3951   CACTCATTCC ACTGAGATGT TTGGTAGGTG GTTGCGGATA GAGGACTTGA
4001   GTTACTCTCA GCTACTTNNA TTTCTTGTGT TTGGGGAAGA TGATCAATCC
```

Fig. 15-3

SEQ ID NO: 3

```
4051 TTAGTCCGGN GTCTTGGATT TTAGNTGNGT TACCATCAGA TTNGCTTTGG
4101 GTGGTGTGAT TTGTAATCTC CATGATATCT CTTAATATTC TCAGGTGACA
4151 TTAGCATTGT ATGTTACTGG GCGAAGTTCC TCGAATAAGG GTTCTTCCCT
4201 AAAGCCTCAT GTCTCAGGAA ATCTTGTACA TGACTGGTAC TAACATAATA
4251 CAATTGTAGA TCTGATACTT TCTTGTTACA CAAAATGTTG TTAAAAGTTA
4301 TATATTTTGA CTCCTGCAAG AGCAAAACTA AGAAATAATC TGGTACTATA
4351 TAGAGTTTGA AACACTGAAT TGGACAAGAT GATTCTATAG AACTTCGTAG
4401 AGTGTTGAGT AATTTCTCCT AGAACGGTTG TAGCTTCCTC TTTTTTCCTT
4451 TTAACCGCAG TGACTTTAGC TTTTGGAACT TTTCTACTGA AACTAGAAGT
4501 TCTGGTTTTG TCTTTCACTT ATCTCTTCCA AACAACTGCT TCAATTTTTT
4551 CTCATATTGT TTGTTTCATG TGATAGGTGG TTTGGAATAC AGCTGAATCC
4601 TCAGTTTATG AGCATTGATC TCAAGTAATC CATTTTTCTG TTTTTTCTTC
4651 TATTTGTCAG CCAAGGCTAC ATCATTGCTT CAGTTTGTTC CGTACTCAAT
4701 CGAGTGGCAG TTTAATAATG TAATCAGCAG TTATGCATGG TTATGATGAA
4751 TGGGAGTTAT TCCTTGTGTA GGTTTTTCTT TGTCAGAGCC GGGATGATGG
4801 GATGGCTGCT TATCAATCTC TCTATTCTGG CAAAAAGTGT GCAGGATGGT
4851 TCCTTGAGTC AGTCGATGAT CTTTACCAGA TCTTCTGTGC GGTAAATTTG
4901 GTTTTTACTT ACAAATCTTG CTTCTTGAAN TCTGATCATC TGTGTTTTGT
4951 TAGTTTTGAT TAGTTTTATA ATTGCAGTTA TATATATTGG ATACTTTGTT
5001 CATGAAGAAT ACATGACCTC TACGTAAGTT CATGGCGTGT TAAGGAAACA
5051 CATTTGTCTT ACCAAAAAAT GACCATTTGC ATTATTACAT CTACTTTGAT
5101 TTTACTCTTT TCAGGTGGGA CATAATTGCA GAGAGACTAG GCTTCATGCT
5151 AGTGTTTGGA GATCTCCTGT GGATTCCTTT CACTTTTAGC ATTCAGGCAT
5201 GTAACTGTGA GCCTGAACAC AAACAAGATA TTAATTTATC TTATTGACAG
5251 TATCTTCTTG GCATGTTACA GTTATTCTCG GAAACAATAT TGTTCTAGAA
5301 TGCTTGATCA CTCTGTGACT GAATTGTCTT CTCTCTGGTA CAGGGCTGGT
5351 GGCTTTTGCA CAACAAAGTA GAACTAACAA TTCCTGCGAT TGTAGTCAAT
```

Fig. 15-4

```
                      SEQ ID NO: 3
5401  TGCCTTGTCT TCTTGATAGG GTAAGTTCTG AGACATGGGG TTATTTTCCA
5451  TTCTTACATA TCTACACTAA GAAACCCACT ATTTCTTCTT TGGCAGGTAC
5501  ATGGTTTTTC GAGGAGCTAA CAAACAAAAA CATATCTTTA AGAAGAACCC
5551  AAAAACACCA ATATGGGGCA AGCCTCCAGT GGTAGTTGGT GGAAAGTTAC
5601  TGGTTTCAGG CTATTGGTAT GTTATATTTA TCTTCTCTTG TTTCTTTGCT
5651  TGGTTTCGCC ATCTCTGTGT TTGATTGTTC ATCATGCTGG GAATAAAGAG
5701  TTGAAAGTTC CGCAATGACA CATTTCCGAT AACTTAGGTG CTGTTTTGTA
5751  TATATGACAG GGGAATTGCA AGGCACTGTA ATTACCTTGG CGACTTGATG
5801  CTTGCTCTGT CCTTCAGTTT GCCATGTGGA ATAAGGTACT CCTNCTGCTT
5851  GAGTTCACTT ACAGCTACCA AAATCATGTA GAAACTAATA CCAATATCNA
5901  AACGTTCGAA GTTGATTTGG CTGACTTAAA GATATTGATC TCTAACCATC
5951  ATTTGAAAAG TCTAAAGCTT TCAAGTTCAT TTCCCAAAGC TGTTTTTATG
6001  ATATTTCGTC TNGTGTATTC TCAGTTCTCC GGTTCCATAT TTCTACCCGA
6051  TATACCTGCT GATACTATTG ATATGGAGAG AACGAAGAGA CGAAGTTCGA
6101  TGTGCAGAGA AGTACNAGGA GATATGGGCA GAGTATCTTA GACTTGTCCC
6151  CTGGAGAATA CTTCCTTATG TTTATTAGAT GTGCCAAGAG CCAATTCATG
6201  AATCCTTTCA GATTCATCCT CTTGTGTCTT ATTTTTTCAT TAAATGTGAC
6251  NTGAAATGAT CCCATTATNG CCTNTTATCA ATGCTTGATT GAAACTTTGT
                           ELL
6301  AGTACACGTT TGAGAATTAC TTCAGTCCTT GTTATTATTT TAGCATGGAT
6351  ATCAACATTT TCGGATTTAT TTNTNGGGTT ATTTAAAAC CNNAGATTAC
6401  CNAANAAAAC CATTGTTTGA NGTANGATAA TATGGACTTT TTACTGAAAA
6451  AAAATNCTAN TAGGGGAACA AATNGAAGTT GAATATGGCT GAATNTTTTT
6501  ATGGANAAAA TGGAAACTTT TCCCACTTTG AAATGACAAT NCAAGTTTGG
6551  TGGACNACTT AATCACTGGA AACGTTAATG GCCAACCN
```

Fig. 15-5

```
  1 CTGAAATTAAACAAAGCGAGAAAAGGCGATACAAACGATTTAGAATGCTT  50   SEQ ID NO: 11
    ||||||||||||||||||||||||||||||||||||||||||||||||||
3356 CTGAAATTAAACAAAGCGAGAAAAGGCGATACAAACGATTTCGAATGCTT 3405  SEQ ID NO: 10

51 CATCTTCTCCTTTGAAAATCCTTCTTCTGCTTAATGCTGCTAGATATGGA 100
    ||||||||||||||||||||||||||||||||||||||||||||||||||
3406 CATCTTCTCCTTTGAAAATCCTTCTTCTGCTTAATGCTGCTAGATATGGA 3455

101 TCTCGGTGTTCTTCTTCCATCATTGCAATCT................... 131
    |||||||||||||||||||||||||||||||
3456 TCTCGGTGTTCTTCTTCCATCATTGCAATCTGTGAGCTGTCTCTTTAGCT 3505

132 ............................GTTTATGTGCTGGTGTTTTAC 152   SEQ ID NO: 12
                                ||||||||||||||||||||||
3556 CTTTTGTTAAATTCGTTCCGAGATTTTAGGTTTATGTGCTGGTGTTTTAC 3605

153 TTCGTTTACTT.GGCCGTTGCCGGAGAAATTCTCCCCGGGAAAGTTATTC 201
    |||||||||||:||:|||||||||||||||||||||||||||||||||||
3606 TTCGTTTACTTGGGNCGNTGGCGGAGAAATTCTCCCCGGGAAAGTTATTC 3655

202 GCGGCGTCCTTTTATCAGATGGCTCTCAACTTCGTTACCGATGCAAT... 248
    |||||||||||||||||||||||||||||||||||||||||||||||
3656 GCGGCGTCCTTTTATCAGATGGCTCTCAACTTCGTTACCGATGCAATGGT 3705

249 ...................................GGTCTATTGGCA 260   SEQ ID NO: 13
                                       ||||||||||||
3756 GAAAGTTCATTTCCATTAGTTTGGTTAATTCAATTTCAGGTCTATTGGCA 3805

261 CTAATATTGTTGGTAGCTATTTTGGGAATCTGTGCAAAACTTGGCATTGT 310
    |||||||||||||||||||||||||:||||||||||||||||||||||||
3806 CTAATATTGTTGGTAGCTATTTNGGGAATCTGTGCAAAACTTGGCATTGT 3855

311 ATCACCTCTT........................................ 320
    ||||||||||
3856 ATCACCTCTTGTAAGTGTAGTTACAAGATTTCGATTGTATTTCTATGAAT 3905

321 .....................GTGGTTGCGGATAGAgGACTTGAgTTAC 348   SEQ ID NO: 14
                         |||||||||||||||||||||||||||
3956 ATTCCACTGAGATGTTTGGTAGGTGGTTGCGGATAGAGGACTTGAGTTAC 4005
```

Fig. 16-1

```
349 TCTCAGCTACTTTTATTTTCTGTGTTT..................... 375
    |||||||||||::|||| |||||||
4006 TCTCAGCTACTTNNATTTCTTGTGTTTGGGGAAGATGATCAATCCTTAGT 4055

376 ...........................TGGTGACATTAgC 388   SEQ ID NO: 15
                               ||||||||||||
4106 GTGATTTGTAATCTCCATGATATCTCTTAATATTCTCAGGTGACATTAGC 4155

389 ATTGTATGTTACTGGGCGAAGTtCCTCgAATAAggGtTctTCCCTAAAgC 438
    |||||||||||||||||||||||||||||||||||||||||||||||||
4156 ATTGTATGTTACTGGGCGAAGTTCCTCGAATAAGGGTTCTTCCCTAAAGC 4205

439 CTCATGTCTCAgGAAATCTTGTACATGACT.................... 468
    |||||||||||||||||||||||||||||
4206 CTCATGTCTCAGGAAATCTTGTACATGACTGGTACTAACATAATACAATT 4255

469 .............GGTGGTTTGGAATACAGCTGAATCCTCAGT 498  SEQ ID NO: 16
                |||||||||||||||||||||||||||||
4556 ATTGTTTGTTTCATGTGATAGGTGGTTTGGAATACAGCTGAATCCTCAGT 4605

499 TTATGAGCATTGATCTCAA............................... 517
    |||||||||||||||||||
4606 TTATGAGCATTGATCTCAAGTAATCCATTTTTCTGTTTTTTCTTCTATTT 4655

518 ..............GTTTTTCTTTGTCAGAGCCGGGATGATGGGATGG 551  SEQ ID NO: 17
                 |||||||||||||||||||||||||||||||||
4756 GTTATTCCTTGTGTAGGTTTTTCTTTGTCAGAGCCGGGATGATGGGATGG 4805

552 CTGCTTATCAATCTCTCTATTCTGGCAAAAAGTGTGCAGGATGGTTCCTT 601
    |||||||||||||||||||||||||||||||||||||||||||||||||
4806 CTGCTTATCAATCTCTCTATTCTGGCAAAAAGTGTGCAGGATGGTTCCTT 4855

602 GAGTCAGTCGATGATTCTTTACCAGATCTTCTGTGC.............. 637
    ||||||||||||| ||||||||||||||||||||||
4856 GAGTCAGTCGATGA.TCTTTACCAGATCTTCTGTGCGGTAAATTTGGTTT 4904

638 ...................GTTATATATATTGGACTACTTTGTTCAT 665  SEQ ID NO: 18
                      |||||||||||||||||||||||||||
4955 TTTGATTAGTTTTATAATTGCAGTTATATATATTGGA.TACTTTGTTCAT 5003
```

Fig. 16-2

```
 666 GAAgAATACATGACCTCTAC............................ 685
     ||||||||||||||||||||
5004 GAAGAATACATGACCTCTACGTAAGTTCATGGCGTGTTAAGGAAACACAT 5053

686 ..........GTGGGACATAATTGCAGAGAGACTAgGCTTCATGCTAGT 724   SEQ ID NO: 19
               |||||||||||||||||||||||||||||||||||||||
5104 ACTCTTTTCAGGTGGGACATAATTGCAGAGAGACTAGGCTTCATGCTAGT 5153

725 GTTTGGAGATCTCCTGTGGATTCCTTTCACTTTTAGCATT.......... 764
     ||||||||||||||||||||||||||||||||||||||||
5154 GTTTGGAGATCTCCTGTGGATTCCTTTCACTTTTAGCATTCAGGCATGTA 5203

765 .....................................CAGGGCTGGTGGC 777   SEQ ID NO: 20
                                          |||||||||||||
5304 TTGATCACTCTGTGACTGAATTGTCTTCTCTCTGGTACAGGGCTGGTGGC 5353

778 TTTTGCACAACAAAGTAgAACTAACAGTTCCTGCGATTGTAGTCAATTGC 827
     ||||||||||||||||| |||||||| |||||||||||||||||||||||
5354 TTTTGCACAACAAAGTAGAACTAACAATTCCTGCGATTGTAGTCAATTGC 5403

828 CTTGTCTTCTTGATAG.................................. 843
     ||||||||||||||||
5404 CTTGTCTTCTTGATAGGGTAAGTTCTGAGACATGGGGTTATTTTCCATTC 5453

844 ..........................................GGTACATG 851   SEQ ID NO: 21
                                                 ||||||||
5454 TTACATATCTACACTAAGAAACCCACTGTTTCTTCTTTGGCAGGTACATG 5503

852 GTTTTTCGAgGAgCTAACAAACAAAAACATATCTTTAAGAAGAACCCAAA 901
     ||||||||| || |||||||||||||||||||||||||||||||||||||
5504 GTTTTTCGAGGAGCTAACAAACAAAAACATATCTTTAAGAAGAACCCAAA 5553

902 AACACCAATATGGGGCAAGCCTCCAGTGGTAGTTGGTGGAAAGTTACTGG 951
     |||||||||||||||||||||||||||||||| |||||||||||||||||
5554 AACACCAATATGGGGCAAGCCTCCAGTGGTACTTGGTGGAAAGTTACTGG 5603

952 TTTCAGGCTATT...................................... 963
     ||||||||||||
5604 TTTCAGGCTATTGGTATGTTATATTTATCTTCTCTTGTTTCTTTGCTTGG 5653

964 ......GGGGAATTGCAAGGCACTGTAATTACCTTGGCGACTTGATGCTT 1007  SEQ ID NO: 22
           ||||||||||||||||||||||||||||||||||||||||||||
5754 ATGACAGGGGAATTGCAAGGCACTGTAATTACCTTGGCGACTTGATGCTT 5803
```

Fig. 16-3

```
1008 GCTCTGTCCTTCAGTTTGCCATGTGGAATA.................... 1037
     ||||||||||||||||||||||||||||||
5804 GCTCTGTCCTTCAGTTTGCCATGTGGAATAAGGTACTCCTNCTGCTTGAG 5853

1038 ...................AGTTCTCCGGTTCCATATTTCTACCCGATAT 1068 SEQ ID NO: 23
                       ||||||||||||||||||||||||||||||||
6004 TTTCGTCTNGTGTATTCTCAGTTCTCCGGTTCCATATTTCTACCCGATAT 6053

1069 ACCTTCTGATACTATTGATATGGAGAGAACGAAGAGACGAGGTTCGATGT 1118
     ||||  |||||||||||||||||||||||||||||||||| |||||||||
6054 ACCTGCTGATACTATTGATATGGAGAGAACGAAGAGACGAAGTTCGATGT 6103

1119 GCAGAGAAGTACAAGGAGATATGGGCAGAGTATCTTAGACTTGTCCCCTG 1168
     |||||||||||||:||||||||||||||||||||||||||||||||||||
6104 GCAGAGAAGTACNAGGAGATATGGGCAGAGTATCTTAGACTTGTCCCCTG 6153

1169 GAGAATACTTCCTTATGTTTATTAGATGTGCCAAGAGCCAAGTCATGAAt 1218
     ||||||||||||||||||||||||||||||||||||||||| ||||||||
6154 GAGAATACTTCCTTATGTTTATTAGATGTGCCAAGAGCCAATTCATGAAT 6203

1219 CCTTTCAGATTCACCTCTTGTTGTCTTATTTTTTCCATAA.......... 1258
     |||||||||||| |   |  |||||||||||| |||
6204 CCTTTCAGATTCATCCTCTTGTGTCTTATTTTTTCATTAAATGTGACNTG 6253

1259 .........TCTTGTTTTATTTTAGCAATGCTCGAATTGAAACTTTGTAG 1299 SEQ ID NO: 24
              || |:   |:|||  ||||||| | ||||||||||||||||
6254 AAATGATCCCATTATNGCCTNTTATCAATGCTTG.ATTGAAACTTTGTAG 6302

1300 TACACTTTTGAAAAATAACTTCAGTCCTT 1328
     ||||| ||||  |  ||| ||||||||||
6303 TACACGTTTG.AGAATTACTTCAGTCCTT 6330
```

Fig. 16-4

PLANT STEROL REDUCTASES AND USES THEREOF

CROSS REFERENCE TO RELATED APPLICATION

This application claims benefit from provisional application No. 60/022,086, filed Jun. 21, 1996.

BACKGROUND OF THE INVENTION

This application relates to plant sterol biosynthetic enzymes, genes, and their uses.

Plant sterols belong to a large group of secondary compounds known as terpenes or isoprenoids. Sterol biosynthesis in plants generally involves a series of different enzymatic steps in the isoprenoid pathway that result in the formation of a variety of sterol end products (Benveniste *Ann. Rev. Biochem.* 37:275, 1986). Although such sterol compounds have been identified in higher plants, their function in plant growth and development is poorly understood.

One such plant sterol, brassinolide, that belongs to a class of sterols referred to as brassinosterioids (BR), was first discovered in the pollen of *Brassica napus* (Grove et. al., *Nature* 281: 216, 1979). Brassinosteroids are growth-promoting natural products having structural similarities to animal steroid hormones. The wide distribution of brassinosteroids in the plant kingdom, their effect on cell proliferation and elongation, and their interactions with other plant hormones (e.g., cytokinins), have indicated that these compounds are plant-growth regulators. Brassinosteroids are thought to promote hypocotyl elongation, leaf unrolling, and xylem differentiation. In addition, such compounds are also believed to be involved in de-etiolation of cotyledons, root elongation, radial growth, and anthocyanin formation.

The function of plant sterol growth regulators, such as BR, in relationship to other classes of plant growth regulators such as auxin, gibberellin, abscisic acid, and cytokinin, during plant development also needs to be evaluated. For example, the growth regulator, cytokinin, is known to affect a variety of developmental processes including photomorphogenesis, chloroplast biogenesis and maintenance, apical dominance, and senescence. In addition, this growth regulator is thought to antagonize BR's ability to promote hypocotyl elongation and cotyledon de-etiolation.

SUMMARY OF THE INVENTION

In general, the invention features a substantially pure plant C-14 sterol reductase polypeptide. Preferably, the C-14 sterol reductase polypeptide includes an amino acid sequence substantially identical to the sequence shown in FIG. 14 (SEQ ID NO: 1); and is from a dicot (for example, a crucifer or a solanaceous plant), monocot, gymnosperm, or an alga.

In related aspects, the invention features purified DNA that includes a sequence encoding a C-14 sterol reductase polypeptide (for example, a sequence substantially identical to the DNA sequence shown in FIG. 14; SEQ ID NO: 2; or a DNA sequence that encodes a C-14 sterol reductase polypeptide which has an amino acid sequence substantially identical to that shown in FIG. 14; SEQ ID NO: 1). The invention also features a vector and a cell, each of which includes purified DNA encoding a C-14 sterol reductase polypeptide; and a method of producing a recombinant C-14 sterol reductase polypeptide involving providing a cell (for example, a plant cell) transformed with purified DNA encoding a C-14 sterol reductase polypeptide positioned for expression in the cell, culturing the transformed cell under conditions for expressing the DNA, and isolating the recombinant C-14 sterol reductase polypeptide. The invention further features recombinant C-14 sterol reductase produced by such expression of a purified DNA, and an isolated antibody that specifically recognizes and binds a plant C-14 sterol reductase polypeptide.

In addition, the invention features nucleotide sequences that hybridize to a C-14 sterol reductase gene (including the coding sequence of such a gene and its complement) and that encode a C-14 sterol reductase polypeptide. Furthermore, the invention includes oligonucleotide probes that detect a C-14 sterol reductase gene or functional equivalents thereof in a plant (for example, dicots (such as solanaceous and cruciferous plants), monocots, gymnosperms, and algae). Such probes are useful to isolate DNA sequences that encode C-14 sterol reductases from other plants. In one particular example, oligonucleotides may be designed based on a C-14 sterol reductase sequence disclosed herein and used as hybridization probes or as primers in polymerase chain reactions (PCR). Conserved regions in the C-14 sterol reductase gene are useful in the design of such primers to facilitate the recovery of C-14 sterol reductases from other related and unrelated plants.

In yet other related aspects, the invention features a transgenic plant (or seeds or cells thereof) containing DNA encoding a C-14 sterol reductase polypeptide integrated into the genome of the plant, where the DNA is expressed in the transgenic plant, resulting in the production of a C-14 sterol reductase polypeptide.

In still another aspect, the invention features a method for reducing the level of a plant C-14 sterol reductase polypeptide in a transgenic plant cell. This method generally involves expressing in the transgenic plant cell an antisense C-14 sterol reductase polypeptide nucleic acid sequence. In general, such an antisense C-14 sterol reductase nucleic acid sequence is encoded by a transgene integrated into the genome of the transgenic plant cell and is based on the nucleotide sequence that is shown in FIG. 14 (SEQ ID NO: 2) or FIG. 15. (SEQ ID NO: 3). In preferred embodiments, the plant cell expressing an antisense C-14 sterol reductase nucleic acid sequence is a dicot (for example, crucifer), monocot, gymnosperm, or algal cell. In yet other preferred embodiments, the method involves growing a transgenic plant from the transgenic plant cell, whereby the level of the C-14 sterol reductase polypeptide is reduced in the transgenic plant.

In other related aspects, the invention features a plant cell expressing an antisense C-14 sterol reductase nucleic acid sequence and a plant expression vector that includes an antisense C-14 sterol reductase nucleic acid sequence, where the antisense sequence is operably linked to an expression control region.

In another aspect, the invention features a method for increasing the level of a C-14 sterol reductase in a transgenic plant cell. This method involves expressing in the transgenic plant cell a C-14 sterol reductase polypeptide nucleic acid sequence. Preferably, the method utilizes a C-14 sterol reductase nucleic acid sequence that is substantially identical to the nucleotide sequence that is shown FIG. 14 (SEQ ID NO: 2). In preferred embodiments, the plant cell expressing a C-14 sterol reductase polypeptide nucleic acid sequence is a dicot (for example, a crucifer), monocot, gymnosperm, or algal cell.

In another aspect, the invention features a transgenic plant having a knockout mutation in DNA encoding a plant C-14 sterol reductase polypeptide. Such knockout genes are constructed according to conventional methods (e.g., Lee et al. *Plant Cell* 2: 415, 1990; Miao and Lam, *Plant J.* 7: 359, 1995).

By "plant C-14 sterol reductase" is meant an amino acid sequence that catalyzes the reduction of any sterol precursor having a C14=C15 double bond, for example, as described by Benveniste, *Annu. Rev. Biochem.* 37: 275, 1986. Preferably, such a polypeptide has an amino acid sequence which is at least 30%, preferably 40%, and most preferably 50% or even 80–95% identical to the amino acid sequence of the C-14 sterol reductase polypeptide shown in FIG. 14 (SEQ ID NO: 1). The length of comparison of amino acid sequences will generally be at least 16 amino acids, preferably at least 20 amino acids, more preferably at least 25 amino acids, and most preferably at least 35 amino acids.

By "polypeptide" or "protein" is meant any chain of amino acids, regardless of length or post-translational modification (for example, glycosylation or phosphorylation).

By a "substantially identical" polypeptide sequence is meant an amino acid sequence that differs only by conservative amino acid substitutions, for example, substitution of one amino acid for another of the same class (e.g., valine for glycine, arginine for lysine, etc.) or by one or more non-conservative substitutions, deletions, or insertions, located at positions of the amino acid sequence that do not destroy the function of the polypeptide (assayed, for example, as described herein).

Sequence identity is typically measured using sequence analysis software (for example, Sequence Analysis Software Package of the Genetics Computer Group (University of Wisconsin Biotechnology Center, 1710 University Avenue, Madison, Wis. 53705), BLAST, or PILEUP/PRETTYBOX programs). Such software matches sequences by assigning degrees of homology to various substitutions, deletions, and other modifications.

By "substantially pure polypeptide" is meant a polypeptide preparation that is at least 60% by weight (dry weight) the compound of interest, for example, the C-14 sterol reductase polypeptide or C-14 sterol reductase-specific antibody. Preferably, the preparation is at least 75%, more preferably at least 90%, and most preferably at least 99%, by weight the compound of interest. Purity can be measured by any appropriate method, for example, column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA that is incorporated into a vector; into an autonomously replicating plasmid or virus; or into the genomic DNA of a prokaryote or eukaryote, or that exists as a separate molecule (for example, a cDNA or a genomic DNA fragment produced by PCR or restriction endonuclease treatment) independent of other sequences. It also includes a recombinant DNA that is part of a hybrid gene encoding one or more additional amino acids.

By a "substantially identical" nucleic acid is meant a nucleic acid sequence that encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions, located at positions of the amino acid sequence that do not destroy the function of the polypeptide (assayed, for example, as described herein). Again, the encoded sequence is at least 30%, more preferably 40%, and most preferably 50%, or even 80 to 95% identical at the amino acid level to the sequence of FIG. 14 (SEQ ID NO: 1). Thus, when nucleic acid sequences are compared, a "substantially identical" nucleic acid sequence is one which is at least 30%, more preferably 40%, and most preferably 50%, or even 80 to 95% identical to the sequence of FIG. 14 (SEQ ID NO: 2). The length of nucleic acid sequence comparison will generally be at least 30 nucleotides, preferably at least 60 nucleotides, more preferably at least 75 nucleotides, and most preferably 110 nucleotides. Again, identity is typically measured using sequence analysis software (for example, Sequence Analysis Software Package of the Genetics Computer Group, University of Wisconsin Biotechnology Center, 1710 University Avenue, Madison, Wis. 53705).

By "isolated antibody" is meant antibody that is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody that recognizes and binds a C-14 sterol reductase polypeptide but which does not substantially recognize and bind other molecules in a sample (e.g., a biological sample) which naturally includes a C-14 sterol reductase. An antibody which "specifically binds" a C-14 sterol reductase is sufficient to detect a C-14 sterol reductase product in such a biological sample using one or more of the standard immunological techniques available to those in the art (for example, Western blotting or immunoprecipitation).

By "an antisense C-14 sterol reductase sequence" is meant a nucleotide sequence that is complementary to a plant C-14 sterol reductase messenger RNA. In general, such an antisense sequence will usually be at least 15 nucleotides, preferably about 15–200 nucleotides, and more preferably 200–2,000 nucleotides in length. The antisense sequence may be complementary to all or a portion of the plant C-14 sterol reductase mRNA nucleotide sequence, and, as appreciated by those skilled in the art, the particular site or sites to which the antisense sequence binds as well as the length of the antisense sequence will vary, depending upon the degree of inhibition desired and the uniqueness of the antisense sequence. By binding to the appropriate target sequence, an RNA-RNA, DNA-DNA, or RNA-DNA duplex is formed. A transcriptional construct expressing a plant C-14 sterol reductase antisense nucleotide sequence includes, in the direction of transcription, a promoter, the sequence coding for the antisense RNA on the sense strand, and a transcriptional termination region. Antisense C-14 sterol reductase sequences may be constructed and expressed as described herein or as described, for example, in van der Krol et al., *Gene* 72: 45, 1988; Rodermel et al., *Cell* 55: 673, 1988; Mol et al., *FEBS Lett.* 268: 427, 1990; Weigel and Nilsson, *Nature* 377: 495, 1995; Cheung et al., *Cell* 82, 383, 1995; and U.S. Pat. No. 5,107,065. In addition, C-14 sterol reductase antisense sequences are useful for the formation of triple helices, where the antisense sequence is bound to a DNA duplex. By binding to the target nucleic acid, C-14 sterol reductase antisense sequences can inhibit the function of the target nucleic acid. This results, for example, in the blocking of transcription, processing of poly A+ addition, replication, translation, or promoting inhibitory mechanisms of the cell, such as RNA degradation. The triple helix-forming and antisense C-14 sterol reductase sequences are useful for selectively suppressing certain cellular functions that are associated with C-14 sterol reductase activity.

By a "transformed cell" is meant a cell into which (or into an ancestor of which) has been introduced, by means of recombinant DNA techniques, a DNA molecule encoding (as used herein) a C-14 sterol reductase polypeptide (for example, a substantially identical DNA encoding the C-14 sterol reductase shown in FIG. 14 (SEQ ID NO: 2)).

By "positioned for expression" is meant that the DNA molecule is positioned adjacent to a DNA sequence which directs transcription and translation of the sequence (for example, facilitates the production of, for example, a plant C-14 sterol reductase polypeptide such as the amino acid sequence shown in FIG. 14 (SEQ ID NO: 1)), or an RNA molecule (for example, an antisense RNA).

By "promoter" is meant a minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements); such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "crucifer" is meant any plant that is classified within the Cruciferae family as commonly described in, e.g., Gray's Manual of Botany American Book Company, N.Y., 1950; *Hortus Third: A Concise Dictionary of Plants Cultivated in the U.S. and Canada*, Macmillan, 1976; or Simmons, N. W., *Evolution of Crop Plants*, 1986. The Cruciferae include many agricultural crops, including, but not limited to, broccoli, cabbage, brussel sprouts, rapeseed, kale, Chinese kale, cauliflower, horseradish, and Arabidopsis.

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "transgene" is meant any piece of DNA that is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell that includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genomes.

Other features and advantages of the invention will be apparent from the following detailed description thereof, and from the claims.

BRIEF DESCRIPTION OF THE DRAWINGS

The drawings will first be described.

FIGS. 1A–1B: wild-type plant; wild-type plant+2ip; ell; and ell+2ip.

FIG. 6A shows, from left to right, that the sepal, petal, stamen, and carpel are shorter in ell (lower row) than wild-type (upper row) plants. FIG. 6B shows, from left to right, the top and side view of wild-type (left) and ell (right) flowers.

FIG. 7A shows ell embryo development at the 32- to 64-cell stage, and FIG. 7B shows that, when wild-type embryos have reached the heart stage, ell embryos are only at the globular stage. As shown in FIG. 7C and FIG. 7D, when the wild-type embryo reached the torpedo stage, the ell mutant embryo was at the heart stage. FIG. 7E shows that apical hooks were not formed in ell embryos. And FIG. 7F shows that ell seeds desiccated without completing the late stages of embryogenesis.

FIG. 10A is a schematic illustration showing the position of a T-DNA insertion into chromosome 3 of Arabidopsis, approximately forty base pairs upstream of the ELL gene, and the exon-intron structure of the C-14 sterol reductase gene. FIG. 10B is a schematic illustration showing the map position of ELL on chromosome 3.

FIG. 11 is a schematic illustration showing a comparison of the predicated ELL amino acid sequence (designated Ath; SEQ ID NO: 1) with C-14 sterol reductase of *Saccharomyces cerevisiae* (Erg24) (SEQ ID NO: 4) and *Schizosaccharomyces pombe* (Pombe), (SEQ ID NO: 5) and C-24 sterol reductase of *Sz. pombe* (Sts1) (SEQ ID NO: 6) and *S. cerevisiae* (Yg1022)(SEQ ID NO: 7).

FIG. 12 is a schematic illustration showing that the predicted ELL amino acid sequence (designated Ath; SEQ ID NO: 1) shares homology to human and chicken lamin B receptor (SEQ ID NO: 8, 9).

FIGS. 14–1 to 14–6 are schematic illustrations showing the nucleotide sequence of an Arabidopsis C-14 sterol reductase (SEQ ID NO: 2) and its deduced amino acid sequence polypeptide (SEQ ID NO: 1).

FIGS. 15–1 to 15–5 are schematic illustrations showing the genomic nucleotide sequence of an Arabidopsis C-14 sterol reductase polypeptide (SEQ ID NO: 3).

FIGS. 16–1 to 16–4 are schematic illustrations showing the sequence comparison between the genomic nucleotide sequence (SEQ ID NO: 3) and cDNA sequences (SEQ ID NO: 2) of an Arabidopsis C-14 sterol reductase.

DETAILED DESCRIPTION OF THE INVENTION

There now follows a description of an Arabidopsis mutant, ell (extra long life), that displays a life span that is at least three times greater than wild-type plants. The ell mutant was isolated by T-DNA tagging methods and was shown to encode a novel C-14 sterol reductase. This example is provided for the purpose of illustrating the invention, and should not be construed as limiting.

Identification and Developmental Effects of the ell Mutation

By screening for mutants displaying BR deficiency or constitutive cytokinin activity, a recessive mutation causing pleiotropic developmental effects was identified according to conventional methods in an Arabidopsis T-DNA insertional mutant collection (Feldmann, *Plant J*. 1:71, 1991; Errampalli et al., *Plant Cell* 3: 149, 1991). This mutant, termed "ell", was found to have a number of developmental abnormalities.

Figure 2:
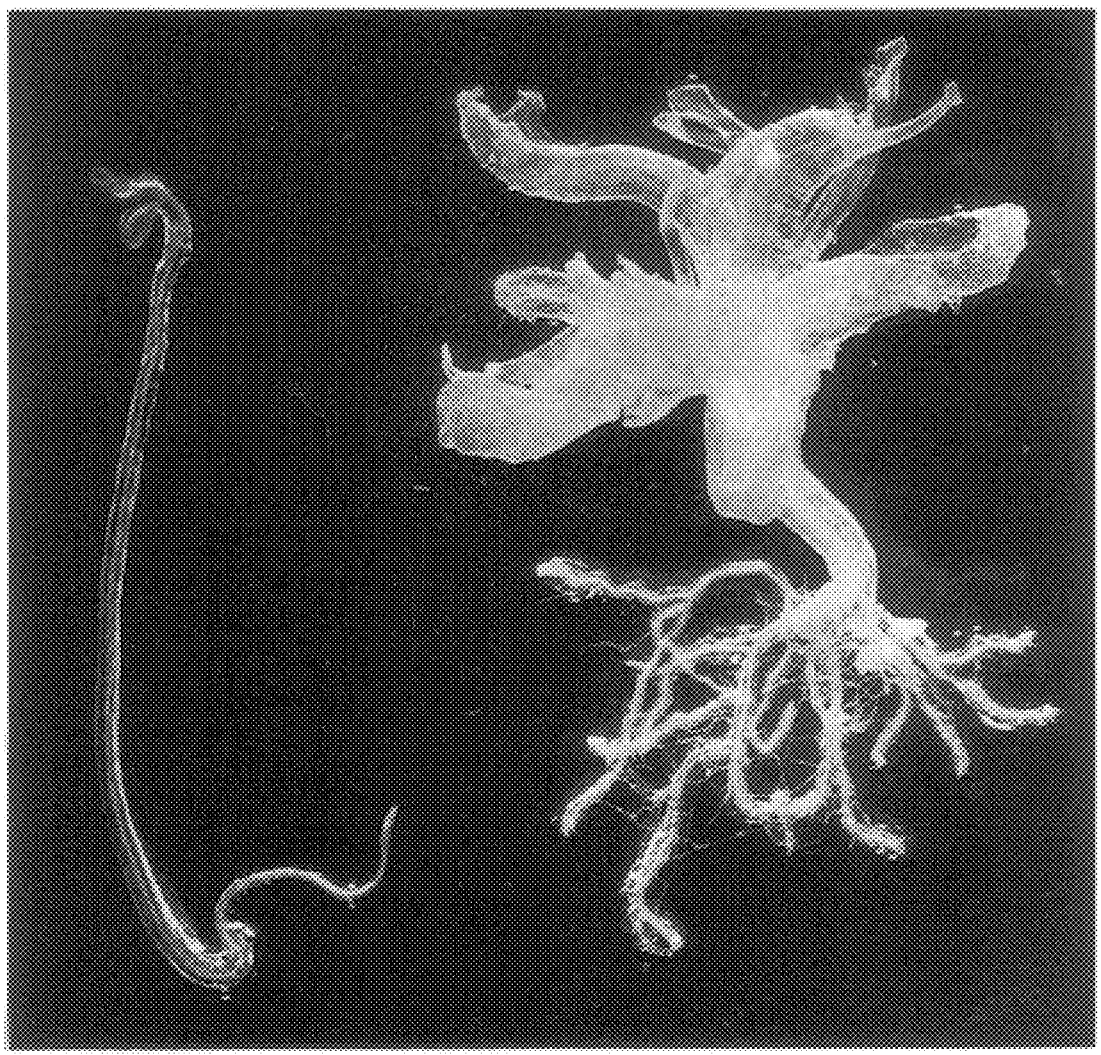
FIG. 2 is a photograph illustrating the constitutive photomorphogenesis of ell seedling development in the dark. Wild-type (left) and ell (right) seedlings were grown in the dark for twenty-one days on Murashige-Skoog (MS) plates containing two percent sucrose.
Figure 3A:
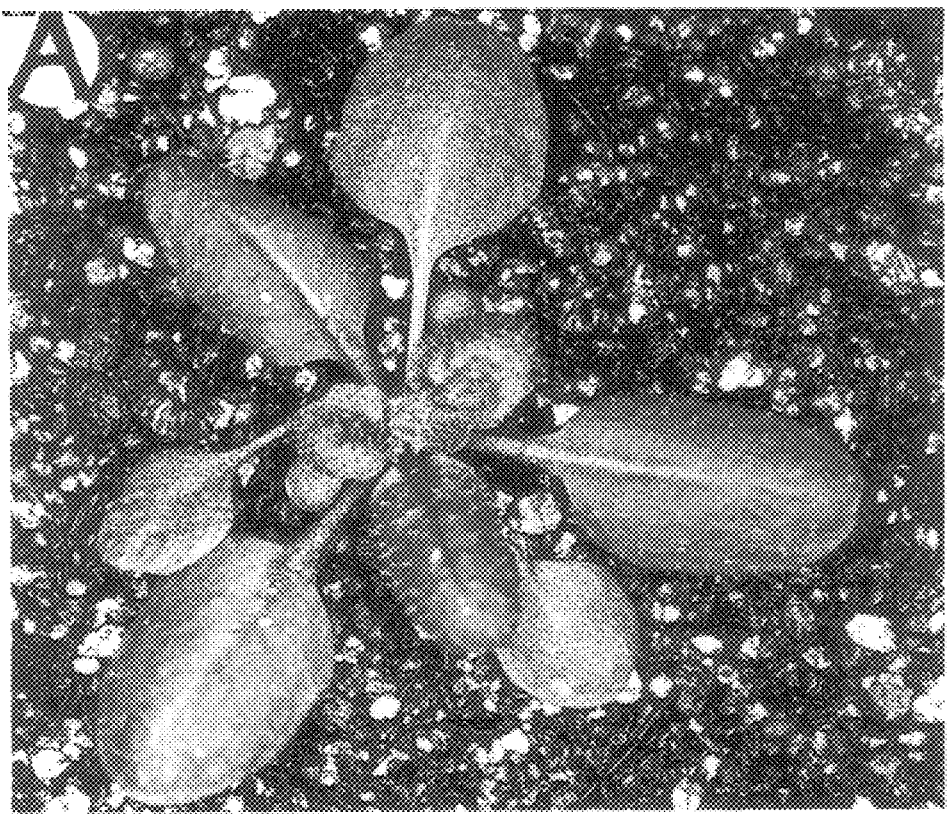
FIGS. 3A–3B are photographs showing that the rosette leaves of the ell plant (FIG. 3B) are darker green in color that those of the wild-type plant (FIG. 3A).
Figure 3B:
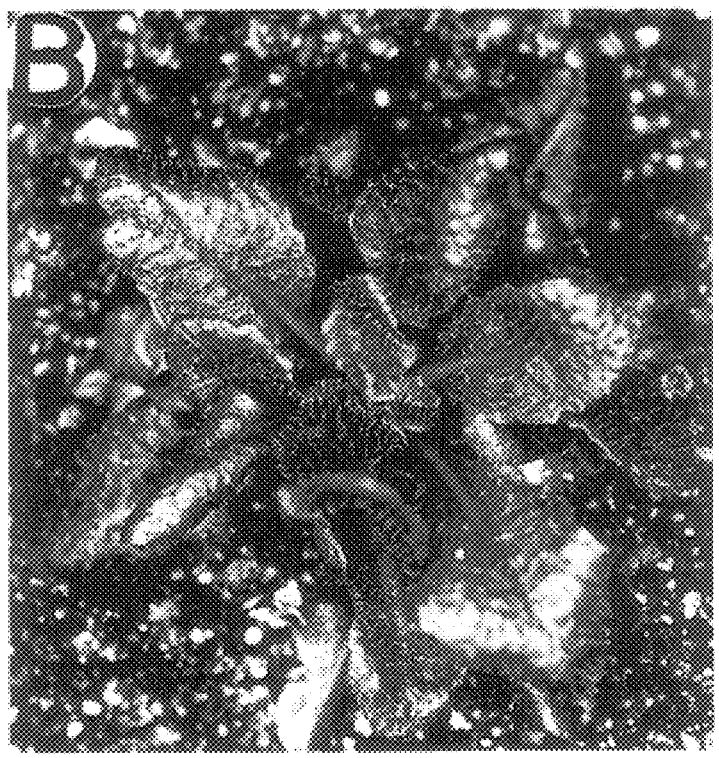
Figure 4:
FIG. 4 is a photograph illustrating that an ell mutant has reduced apical dominance in comparison to a wild-type plant. Six-week-old wild-type (left) and ten-week-old ell (right) plants were grown in the greenhouse.
Figure 5:
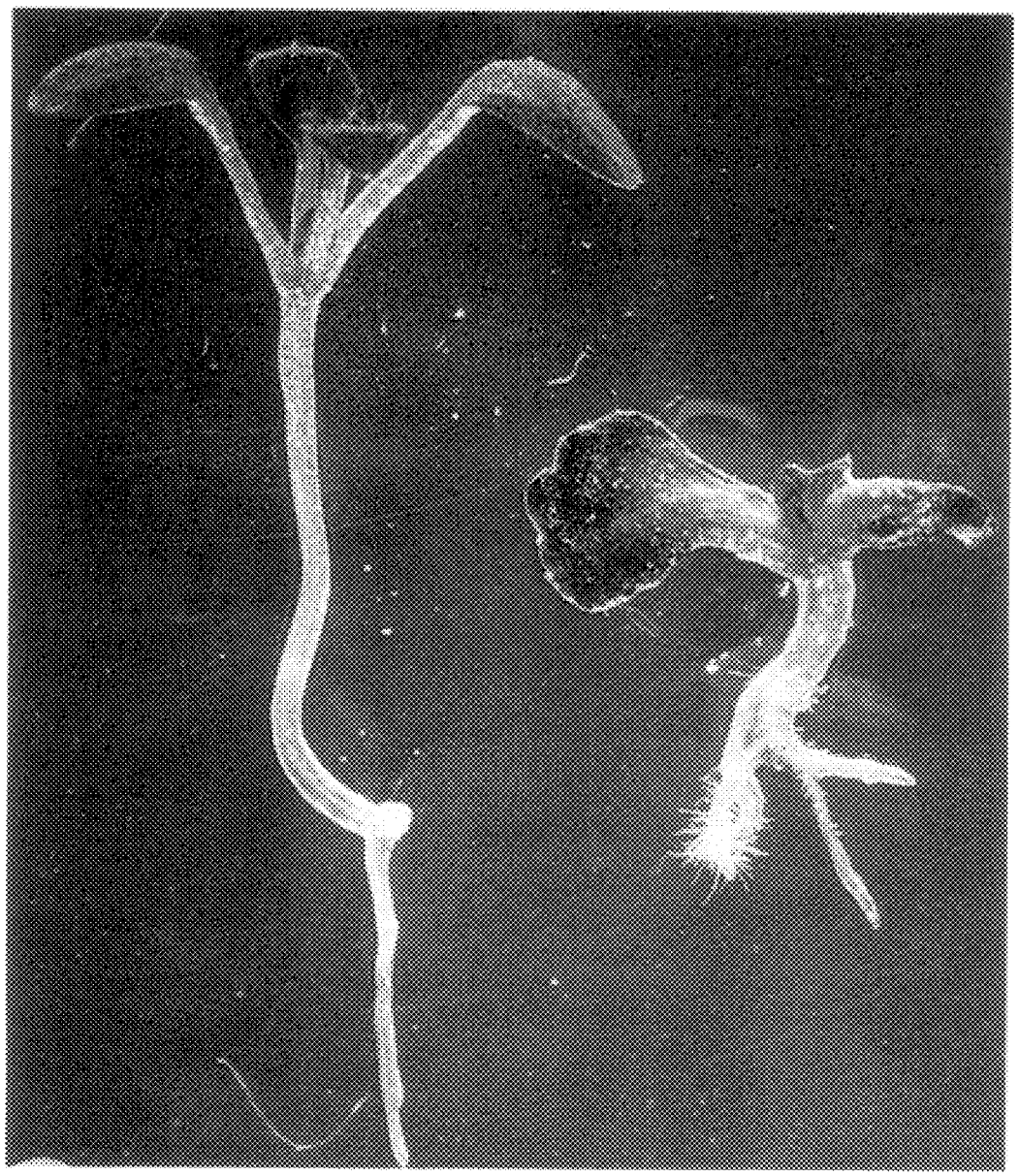
FIG. 5 is a photograph showing that ell mutants (right) exhibit irregular, thickened cotyledons and hypocotyls, and reduced cotyledon petioles compared to wild-type plants (left).
Figure 6A:
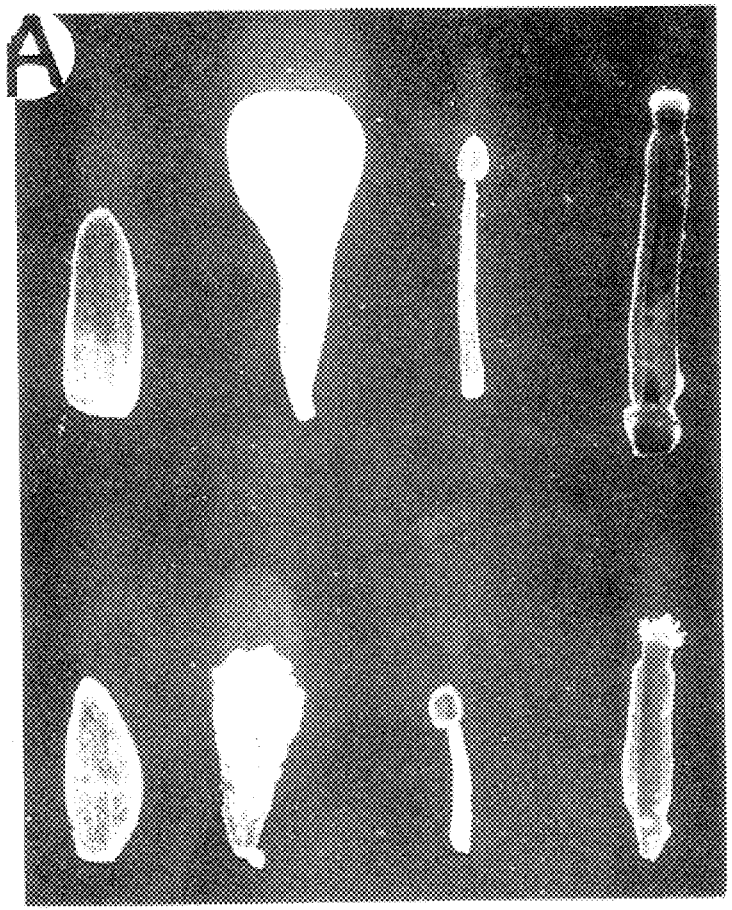
FIGS. 6A–6B are photographs showing abnormal flower development in the ell mutant.
Figure 6B:
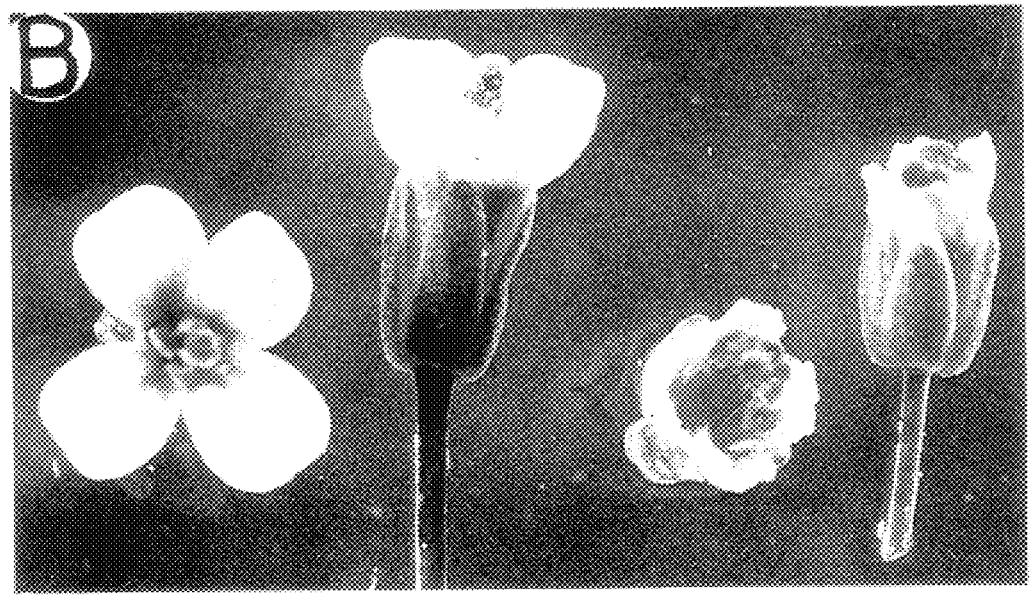
Figure 7A:
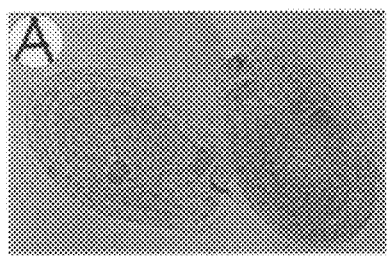
FIGS. 7A–7F are photographs showing embryo development in ell and wild-type plants. Wild-type and ell plants are shown in the left and right of each photograph, respectively.
Figure 7D:
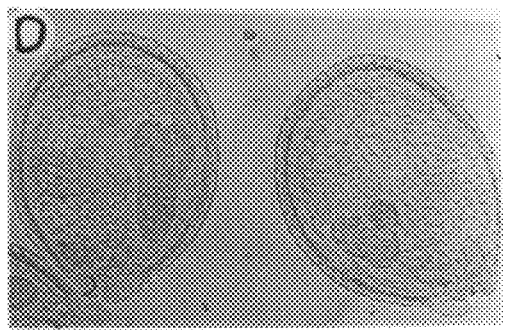
Figure 7B:
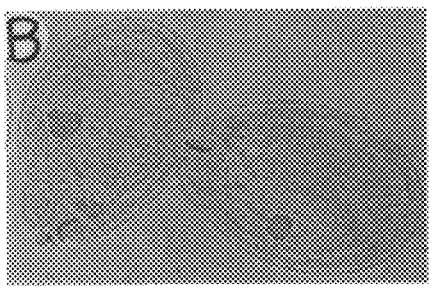
Figure 7E:
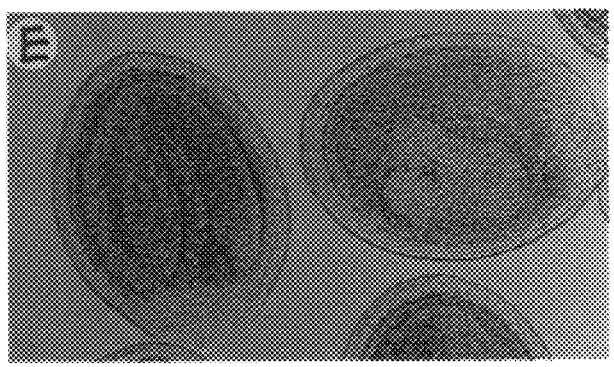
Figure 7C:
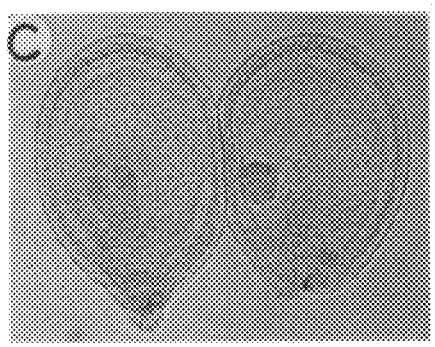
Figure 7F:
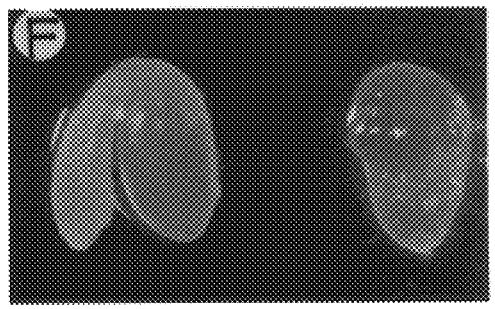
Figure 8A:
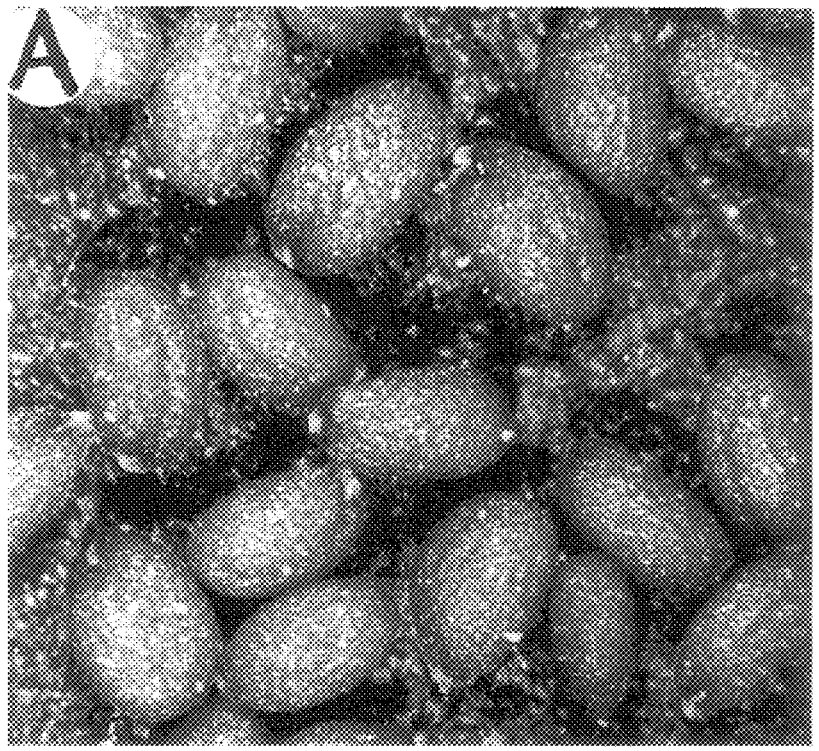
FIGS. 8A–8B are photographs of dry seeds from wild-type (FIG. 8A) and ell plants (FIG. 8B). Reduced seed size, wrinkled seed coat, and precocious germination were observed in ell seeds.
Figure 8B:
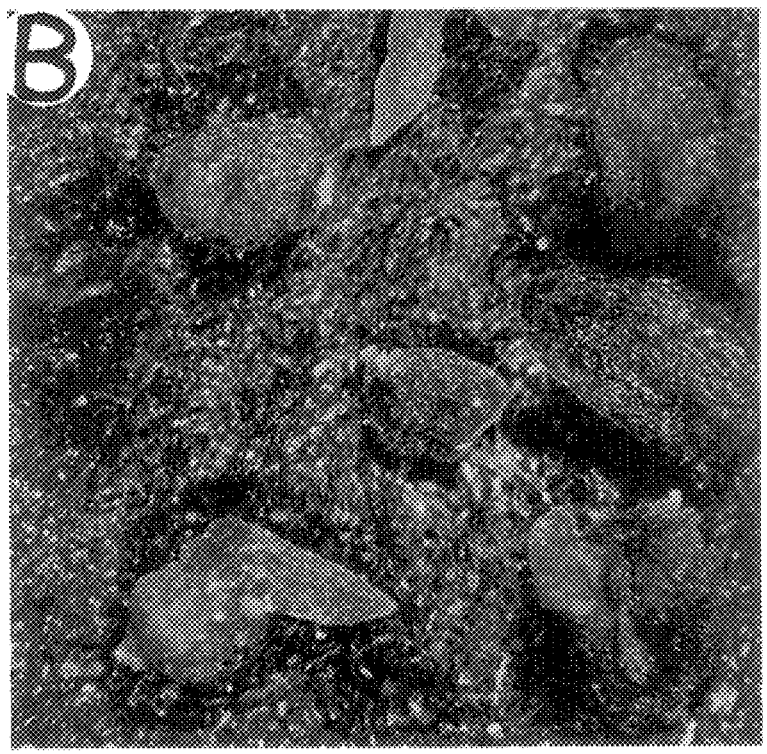
Figure 9A:
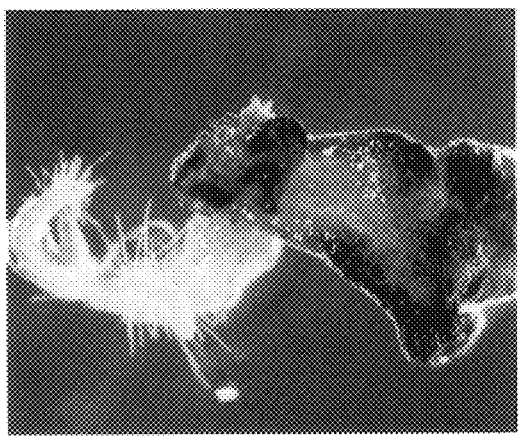
FIGS. 9A–9F are photographs showing the supernumerary cotyledons that were observed in the ell mutant, including one (FIG. 9A), two (FIG. 9B), three (FIG. 9C), four (FIG. 9D), five (FIG. 9E), and more than six cotyledons (FIG. 9F).
Figure 9B:
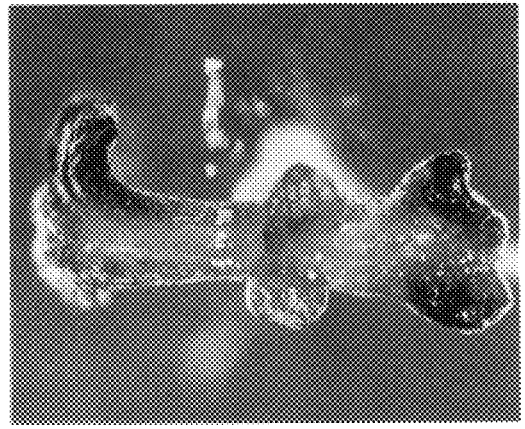
Figure 9C:
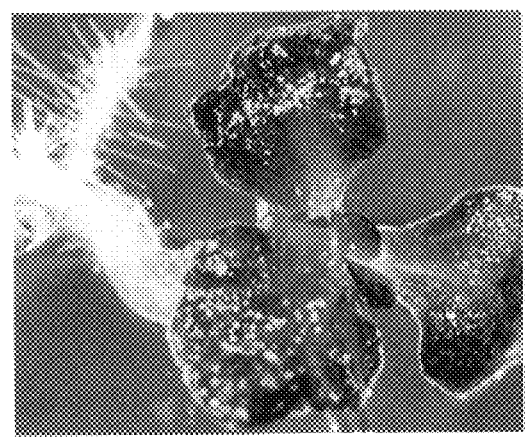
Figure 9D:
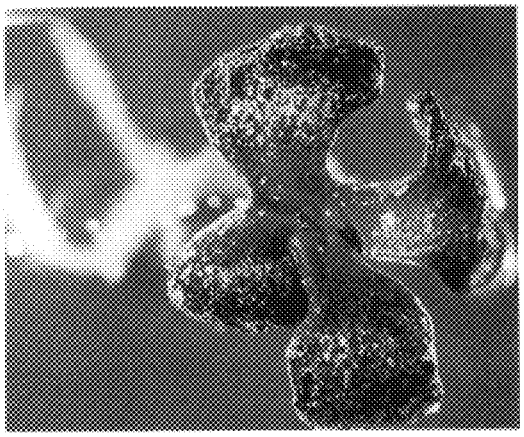
Figure 9E:
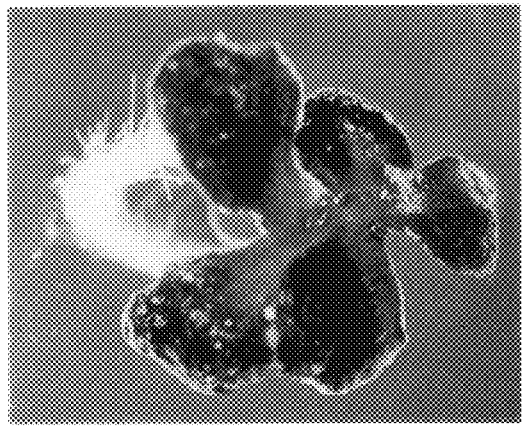
Figure 9F:
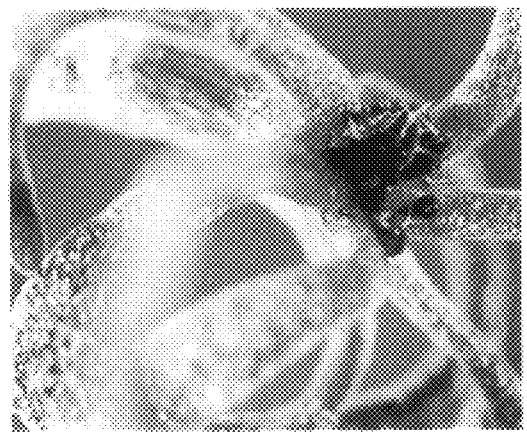

For example, unlike wild-type plants, ell mutants displayed constitutive light-morphogenesis (FIG. 2), similar to the Arabidopsis det2 (Chory et al., *Plant Cell* 3: 445, 1991) and cpd (Szekeres et al., *Cell* 85: 171, 1996) mutants. In addition, compared to wild-type plants, ell plants had darker green rosette leaves (FIGS. 3A–3B), reduced apical dominance (FIG. 4), stunted hairy roots, and irregular hypocotyl and cotyledons (FIG. 5). Furthermore, as shown in FIGS. 6A–6B, the ell mutant showed reduced and ruffled sepals and petals. The ell mutant also showed delayed and altered embryo development (FIGS. 7A–7F) and was found to have reduced fertility, producing wrinkled seeds that precociously germinated (FIGS. 8A–8B). In addition, the various phenotypes of ell overlapped with amp-1 (pt1) (Chaudhury et. al., *Plant J*. 4: 907, 1993) and häuptling (Jürgens et al.,*Ann. Rev. Genet*. 28: 351, 1994), including supernumerary cotyledons (FIGS. 9A–9F).

Figure 1A:
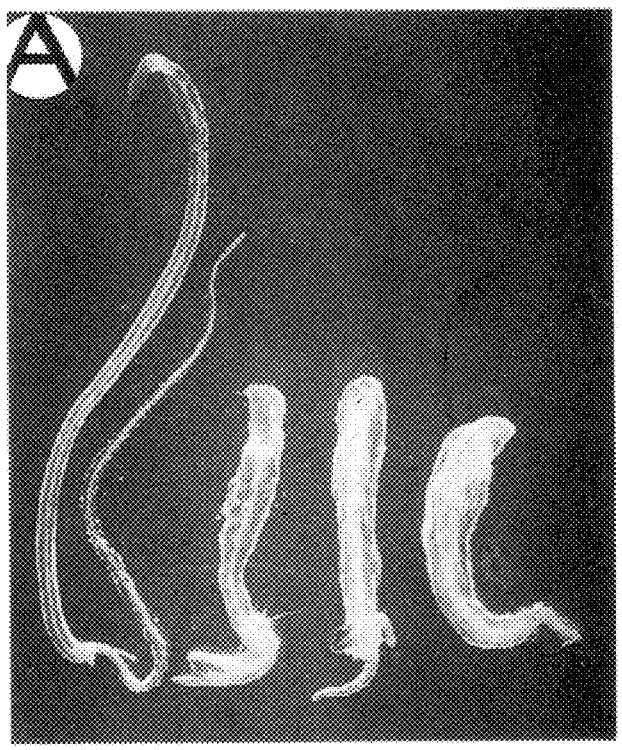
FIGS. 1A–1B are photographs showing that the ell mutant morphology was phenocopied by treating wild-type seedlings with 30 $\mu$M of dimethylallylamino-purine (2ip), a synthetic cytokinin, in the dark (FIG. 1A) or light (FIG. 1B). From left to right in both
Figure 1B:

Finally, as shown in FIGS. 1A–1B, the morphology of the T-DNA tagged ell mutant seedlings was phenocopied by treating wild-type seedlings with 30 μM dimethylallylamine purine (2ip), a synthetic cytokinin.

Despite having a number of developmental abnormalities, ell mutants were found to have a life span that was at least three times greater than wild-type plants.

Genetic Analysis and Molecular Cloning of ELL

Standard segregation analysis indicated that ell is a recessive mutation. The T2 population of the transgenic line carrying the ell mutant showed a 3:1 Mendelian segregation of the T-DNA using kanamycin resistance ($kan^r$) as a selectable marker. Of the $kan^r$ plants, thirty-three percent showed the ell phenotype, indicating that the ell mutation was recessive. A T3 population was then generated from selfed T2 $kan^r$ plants having the wild-type phenotype, and the $kan^r$ marker showed a 3:1 segregation. Of the seventy-five percent displaying $kan^r$, twenty-five percent showed the ell phenotype. Because ell homozygous plants were found to be either lethal or sterile, T2 heterozygous ell plants were subsequently backcrossed to wild-type plants for additional segregation analysis. The resulting F1 population from this backcross showed a 1:1 segregation of the $kan^r$ marker; no plants were observed having the ell phenotype. The F1 $kan^r$ individuals of the backcross were then selfed to produce an F2 population. Seventy-five percent of this F2 population was found to be $kan^r$, and thirty-three percent of the $kan^r$ resistant plants showed the ell phenotype, confirming the recessive nature of this mutant. Consistent segregation of the ell phenotype and $kan^r$ marker was also observed in a subsequent backcross, further indicating that ell was tagged by the T-DNA.

Genomic DNA blot analysis, using an NPTII probe derived from the T-DNA vector, showed that a unique single copy of T-DNA was integrated into the ell genome. This result, together with the segregation data described above, further indicated that the ell phenotype was associated with the $kan^r$ marker, and that the ell mutation resulted from a single T-DNA insertion in the Arabidopsis genome.

Figure 10A:
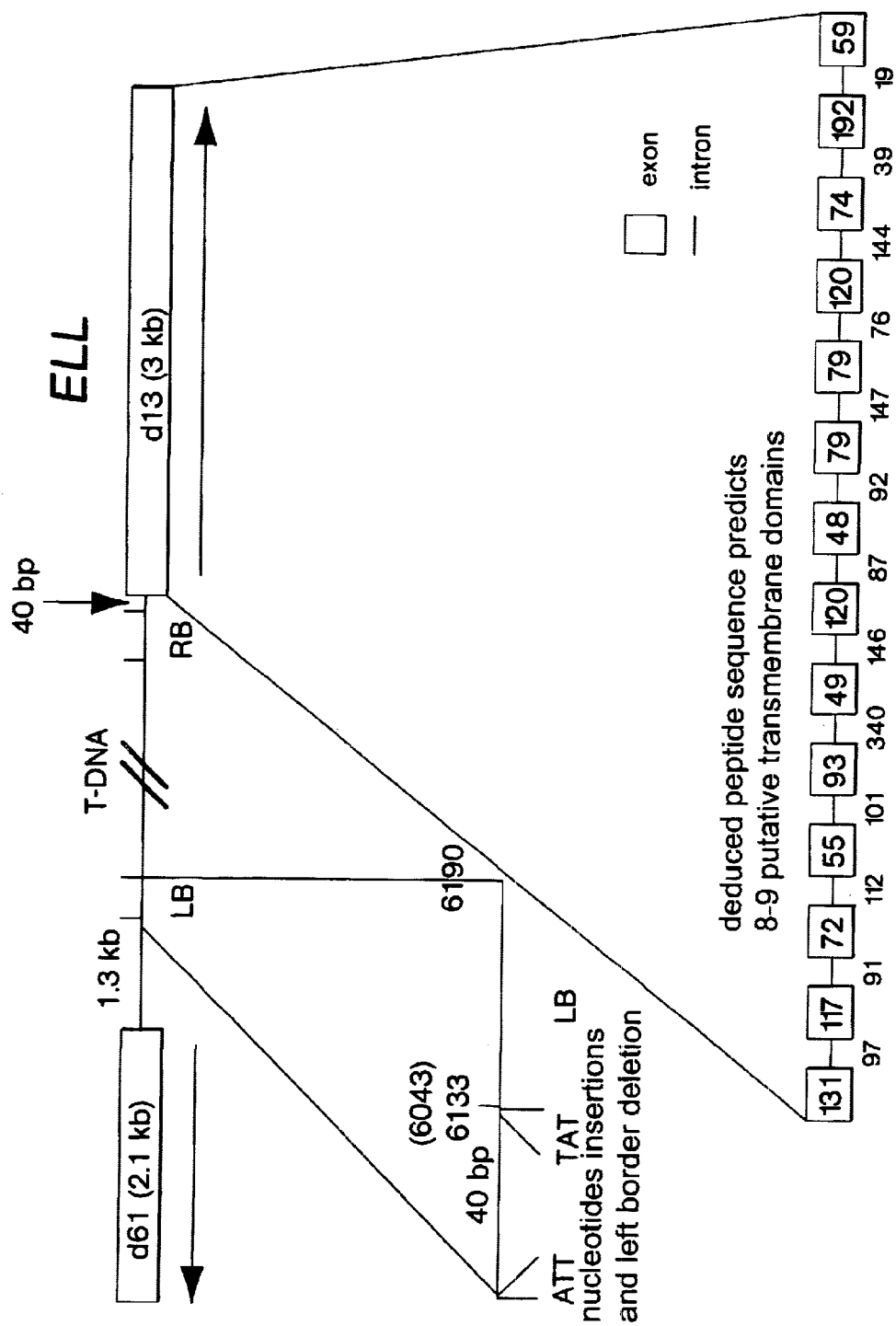
FIGS. 10A–10B are illustrations showing various aspects of the molecular characterization of the *Arabidopsis thaliana* C-14 sterol reductase gene.

The T-DNA-tagged locus was then isolated by constructing a genomic DNA library from the ell mutant and was mapped by hybridization using the NPTII probe. FIG. 10A shows the physical map of the T-DNA tagged locus that was determined by DNA hybridization. One of three genomic clones that were found to hybridize to the NPTII probe was partially sequenced and found to have a complete T-DNA insertion and flanking plant sequences. A segment of this genomic clone containing both T-DNA and plant sequences was then used to screen a genomic library that was prepared from wild-type plants. Two positive clones that were identified in this screen were then sequenced. The genomic nucleotide sequence is presented in FIGS. 15–1 to 15–5 (SEQ ID NO: 3).

The T-DNA-plant DNA insert junctions were also used as probes to screen a cDNA library that was prepared from wild-type plants. One isolated cDNA clone, designated D13, was found to have a nucleotide sequence (SEQ ID NO: 1) that matched the genomic sequences flanking the right T-DNA border. Comparison of the cDNA (FIGS. 14–1 to 14–6) with the genomic DNA sequence (FIGS. 15–1 to 15–5) also revealed that the T-DNA was inserted at a location forty base pairs upstream of the 5' end of the ELL cDNA transcript (FIGS. 16–1 to 16–4). The complete genomic fragment covering the cDNA sequence was composed of 14 exons and 13 introns (FIG. 10A). Probes that were prepared from both the cDNA or genomic clone were then used for DNA blot analysis. Results from this analysis confirmed that the ELL gene was of plant origin.

Figure 10B:
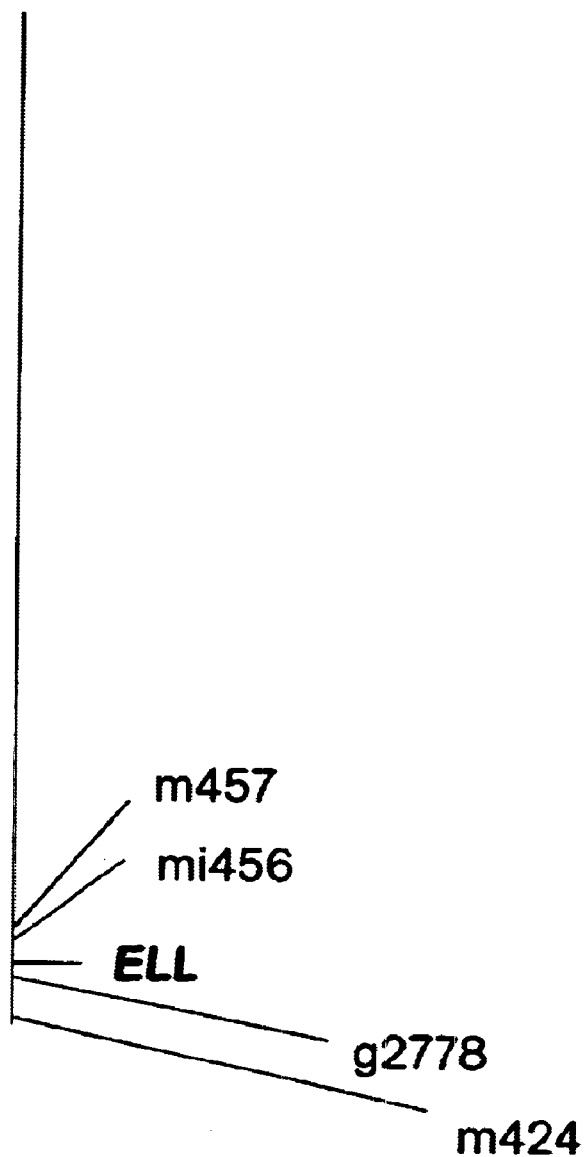

We also determined the chromosomal position of ELL by standard segregation analysis of restriction fragment length polymorphisms (RFLPs) in recombinant inbred lines (Nam et al., *Plant Cell* 1: 699, 1989; Lister and Dean, *Plant J*. 4: 745, 1993; Hauge et al., *Plant J*. 3: 745, 1993; Schmidt et al.,

*Science* 270: 480, 1995; Zachgo et al., *Genomic Res.* 6: 19, 1996). By this analysis, we found that ELL is located on chromosome 3 and is flanked by the chromosomal markers by mi456 and g2778 (FIG. 10B).

ELL Encodes a Novel C-14 Sterol Reductase

Figure 12:
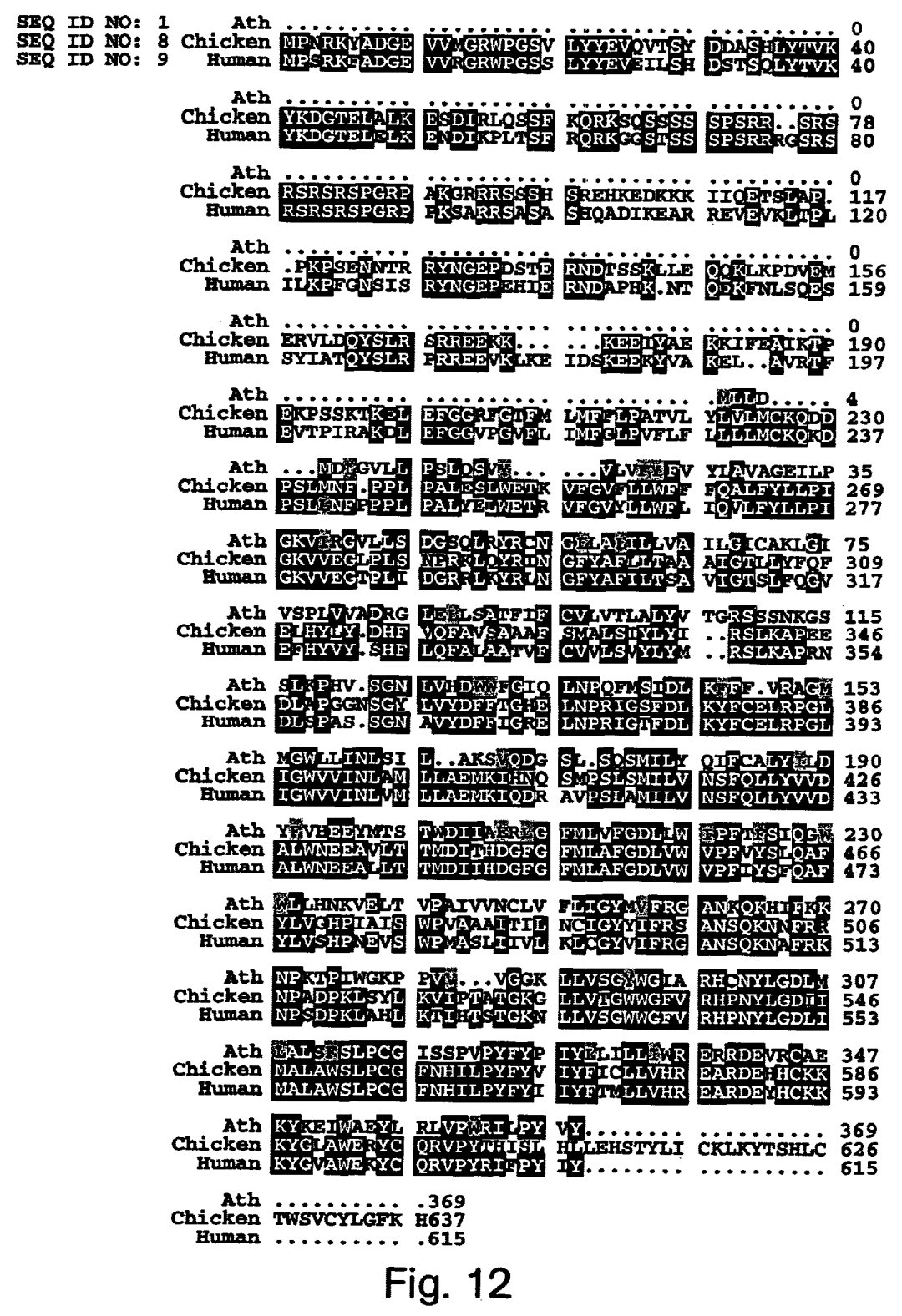

A comparison of the deduced polypeptide sequence of the full-length ELL cDNA clone to the GenBank database showed that ELL had 35% identity to C-14 sterol reductase (Erg24) in yeast (Lorenz and Parks, DNA *Cell Biol.* 9: 685, 1992; Lai et al., *Gene* 140: 41, 1994) (FIG. 11) and 40% identity to the lamin B receptor (LBR) in humans (Ye and Worman, *J. Biol. Chem.* 269: 11306, 1994) (FIG. 12). In addition, the amino acid sequence of ELL predicted several hydrophobic regions and between eight to nine transmembrane domains, consistent with the yeast Erg24 and human LBR. However, ELL was observed to lack a basic nucleoplasmic amino-terminal domain of about 200 amino acids that has been identified in human LBR. Database searches also revealed that at least two Arabidopsis expression sequence tagged (EST) clones (GenBank accession numbers T45011 and T42407) shared homology to ELL. DNA sequencing revealed that T45011 encodes an unknown gene with 60% nucleotide sequence identity to ELL. The predicted amino acid sequence of T45011 was also observed to have greater than 50% identity to the yeast ERG24 and human LBR. These results further confirmed that ELL is encoded by a gene that is a member of the C-14 sterol reductase gene family. T42407 was found to encode an Arabidopsis sterol Δ7-reductase (Lecain et al., *J. Biol. Chem.* 271: 10866, 1996) that shares 32% amino acid identity to ELL.

RNA blot analysis indicated multiple transcripts hybridizing to the full-length ELL cDNA.

Figure 13A:
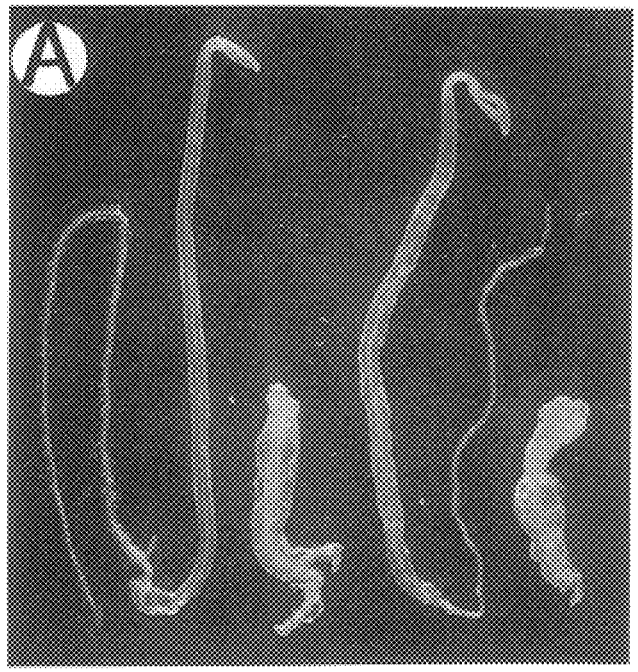
FIGS. 13A–13B are photographs showing that the ell phenotype was not corrected by exogenous feeding of brassinolide (1 μM) in either dark (FIG. 13A) or light (FIG. 13B). From left to right in FIGS. 13A–13B: wild-type; ell; wild-type+brassinolide; and ell+brassinolide.
Figure 13B:
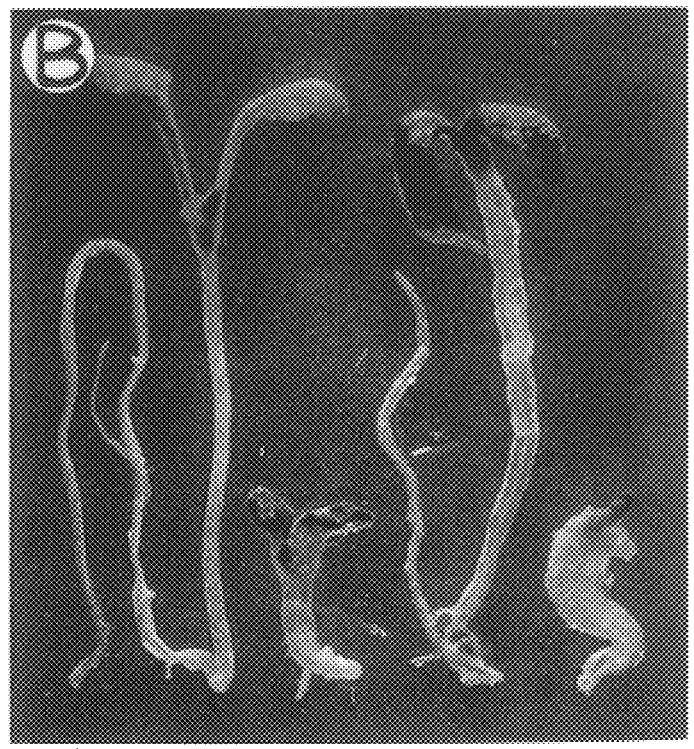

To determine whether the ell mutant phenotype is corrected by exogenous feeding of brassinolide, we germinated ell seedlings on agar plates containing 1 μM brassinolide or 1 μM 24-epibrassinolide (Li et al., *Science* 272: 398, 1996). The results of these experiments showed that the presence of brassinolide or 24-epibrassinolide, in the growth medium of ell plants did not alter the mutant phenotype (FIGS. 13A–13B). Thus, it appears that steroid compounds other than BRs are needed to restore an ell mutant to a normal growth and development phenotype, as reflected by the pleiotropic phenotypes such as stunted roots (FIG. 2) and impaired embryogenesis (FIGS. 7A–7F).

To confirm that ELL activity was upstream of DET2 in the sterol biosynthesis pathway, a double mutant between ell and det2 was constructed and analyzed. The phenotype of det2/ell was indistinguishable from ell, further supporting the hypothesis that DET2 was epistatic to ELL.

Isolation of Other C-14 Sterol Reductase cDNAs and Genomic DNAs

Based on the C-14 sterol reductase genes and polypeptides described herein, the isolation of additional plant C-14 sterol reductase coding sequences is made possible using standard strategies and techniques that are well known in the art. For example, using all or a portion of the amino acid sequence of a C-14 sterol reductase polypeptide, one may readily design C-14 sterol reductase-specific oligonucleotide probes, including C-14 sterol reductase degenerate oligonucleotide probes (i.e., a mixture of all possible coding sequences for a given amino acid sequence). These oligonucleotides may be based upon the sequence of either DNA strand and any appropriate portion of the C-14 sterol reductase sequence (for example, FIGS. 14–1 to 14–6; SEQ ID NOS: 2 and 1, respectively; and FIGS. 15–1 to 15–5 (SEQ ID NO: 3). General methods for designing and preparing such probes are provided, for example, in Ausubel et al., 1996, Current Protocols in *Molecular Biology*, Wiley Interscience, New York, and Berger and Kimmel, *Guide to Molecular Cloning Techniques*, 1987, Academic Press, New York. These oligonucleotides are useful for C-14 sterol reductase gene isolation, either through their use as probes capable of hybridizing to C-14 sterol reductase complementary sequences or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); and Sambrook et al., *Molecular Cloning: A Laboratory Manual*, Cold Spring Harbor Laboratory Press, New York. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

For detection or isolation of closely related C-14 sterol reductase sequences having greater than 80% identity, high stringency conditions are preferably used; such conditions include hybridization at about 65° C. and about 50% formamide, a first wash at about 65° C., about 2×SSC, and 1% SDS, followed by a second wash at about 65° C. and about 0.1% SDS, and 0.1×SSC. Lower stringency conditions for detecting C-14 sterol reductase genes having about 40–50% sequence identity to the C-14 sterol reductase genes described herein include, for example, hybridization at about 37° C. in the absence of formamide, a first wash at about 37° C., about 6×SSC, and about 1% SDS, and a second wash at about 37° C., about 6×SSC, and about 1% SDS. These stringency conditions are exemplary; other appropriate conditions may be determined by those skilled in the art.

As discussed above, C-14 sterol reductase oligonucleotides may also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, C-14 sterol reductase sequences may be isolated using the PCR "RACE" technique, or Rapid Amplification of cDNA Ends (see, e.g., Innis et al. (supra)). By this method, oligonucleotide primers based on a C-14 sterol reductase sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85: 8998, 1988.

Alternatively, any plant cDNA expression library may be screened by functional complementation of a yeast C-14 reductase mutant (for example, the erg24 mutant described by Lorenz and Parks, *DNA Cell Biol.* 9: 685, 1992) according to standard methods.

Useful C-14 sterol reductase sequences may be isolated from any appropriate organism. Confirmation of a sequence's relatedness to the C-14 sterol reductase polypeptide family may be accomplished by a variety of conventional methods including, but not limited to, functional complementation assays and sequence comparison. In addition, the activity of any C-14 sterol reductase sequence may be evaluated according to any of the techniques described herein.

C-14 Sterol Reductase Polypeptide Expression

C-14 sterol reductase polypeptides may be produced by transformation of a suitable host cell with all or part of a C-14 sterol reductase cDNA (for example, the cDNA described above) in a suitable expression vehicle or with a plasmid construct engineered for increasing the expression of a C-14 sterol reductase polypeptide (supra) in vivo.

Those skilled in the field of molecular biology will understand that any of a wide variety of expression systems may be used to provide the recombinant protein. The precise host cell used is not critical to the invention. The C-14 sterol reductase protein may be produced in a prokaryotic host, for example, *E. coli*, or in a eukaryotic host, for example, *Saccharomyces cerevisiae*, mammalian cells (for example, COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include, but are not limited to, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Maize, Millet, Onion, Barley, Orchard grass, Oat, Rye, and Wheat.

Such cells are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; and Gasser and Fraley, *Science* 244: 1293, 1989.

For prokaryotic expression, DNA encoding a C-14 sterol reductase polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., *Nature* 198: 1056, 1977), the tryptophan (Trp) (Goeddel et al., *Nucl. Acids Res.* 8: 4057, 1980), and the tac promoter systems, as well as the lambda-derived $P_L$ promoter and N-gene ribosome binding site (Simatake et al., *Nature* 292: 128, 1981).

One particular bacterial expression system for C-14 sterol reductase polypeptide production is the *E. coli* pET expression system (Novagen, Inc., Madison, Wis.). According to this expression system, DNA encoding a C-14 sterol reductase polypeptide is inserted into a pET vector in an orientation designed to allow expression. Since the C-14 sterol reductase gene is under the control of the T7 regulatory signals, expression of C-14 sterol reductase is induced by inducing the expression of T7 RNA polymerase in the host cell. This is typically achieved using host strains which express T7 RNA polymerase in response to IPTG induction. Once produced, recombinant C-14 sterol reductase polypeptide is then isolated according to standard methods known in the art, for example, those described herein.

Another bacterial expression system for C-14 sterol reductase polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

For eukaryotic expression, the method of transformation or transfection and the choice of vehicle for expression of the C-14 sterol reductase polypeptide will depend on the host system selected. Transformation and transfection methods are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., *Proc. Natl. Acad. Sci., U.S.A* 87: 1228, 1990; Potrykus, I., *Annu. Rev. Plant Physiol. Plant Mol. Biology* 42: 205, 1991; and BioRad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

Most preferably, an C-14 sterol reductase polypeptide is produced by a stably-transfected plant cell line, a transiently-transfected plant cell line, or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, environmentally- or developmentally-regulated, or cell- or tissue-specific expression), a transcription initiation start site, a ribosome binding site, an RNA processing signal, a transcription termination site, and/or a polyadenylation signal.

Alternatively, the C-14 sterol reductase polypeptide may be produced using a transient expression system (e.g., the maize transient expression system described by Sheen, *Plant Cell* 2: 1027, 1990).

Once the desired C-14 sterol reductase nucleic acid sequences is obtained, it may be manipulated in a variety of ways known in the art. For example, where the sequence involves non-coding flanking regions, the flanking regions may be subjected to mutagenesis.

The C-14 sterol reductase DNA sequence of the invention may, if desired, be combined with other DNA sequences in a variety of ways. The C-14 sterol reductase DNA sequence of the invention may be employed with all or part of the gene sequences normally associated with the C-14 sterol reductase protein. In its component parts, a DNA sequence encoding a C-14 sterol reductase protein is combined in a DNA construct having a transcription initiation control region capable of promoting transcription and translation in a host cell.

In general, the constructs will involve regulatory regions functional in plants which provide for modified production of C-14 sterol reductase protein as discussed herein. The open reading frame coding for the C-14 sterol reductase protein or functional fragment thereof will be joined at its 5' end to a transcription initiation regulatory region such as the sequence naturally found in the 5' upstream region of the C-14 sterol reductase structural gene. Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by the DNA sequence encoding the C-14 sterol reductase protein or any convenient transcription termination region derived from a different gene source. The transcript termination region will contain preferably at least 1–3 kb of sequence 3' to the structural gene from which the termination region is derived. Plant expression constructs having C-14 sterol reductase as the DNA sequence of interest for expression (in either the sense or antisense orientation) may be employed with a wide variety of plant life, particularly plant life involved in the production of storage reserves (for example, those involving carbon and nitrogen metabolism). Such genetically-engineered plants are useful for a variety of industrial and agricultural applications as discussed below. Importantly, this invention is applicable to dicotyledons and monocotyledons, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313: 810 1985). The CaMV promoter is also highly active in monocots (see, e.g., Dekeyser et al., *Plant Cell* 2: 591, 1990; Terada and Shimamoto, *Mol. Gen. Genet.* 220: 389, 1990). Moreover, activity of this promoter can be further increased (i.e., between 2–10 fold) by duplication of the CaMV 35S promoter (see e.g., Kay et al., *Science* 236: 1299, 1987; Ow et al., *Proc. Natl. Acad. Sci., U.S.A.* 84: 4870, 1987; and Fang et al., *Plant Cell* 1: 141, 1989).

Other useful plant promoters include, without limitation, the nopaline synthase promoter (An et al., *Plant Physiol.* 88: 547, 1988) and the octopine synthase promoter (Fromm et al., *Plant Cell* 1: 977, 1989).

For certain applications, it may be desirable to produce the C-14 sterol reductase gene product in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88: 965, 1988; Takahashi and Komeda, *Mol. Gen. Genet.* 219: 365, 1989; and Takahashi et al. Plant J. 2: 751, 1992), light-regulated gene expression (e.g., the pea rbcS-3A described by Kuhlemeier et al., *Plant Cell* 1: 471, 1989; the maize rbcS promoter described by Schafffier and Sheen, *Plant Cell* 3: 997, 1991; or the cholorphyll a/b-binding protein gene found in pea described by Simpson et al., *EMBO J.* 4: 2723, 1985), hormone-regulated gene expression (for example, the abscisic acid (ABA) responsive sequences from the Em gene of wheat described by Marcotte et al., *Plant Cell* 1: 969, 1989; the ABA-inducible HVA1 and HVA22, and rd29A promoters described for barley and Arabidopsis by Straub et al., *Plant Cell* 6: 617, 1994, Shen et al., *Plant Cell* 7: 295, 1995; and wound-induced gene expression (for example, of wunI described by Siebertz et al., *Plant Cell* 1: 961, 1989), or organ-specific gene expression (for example, of the tuber-specific storage protein gene described by Roshal et al., *EMBO J.* 6: 1155, 1987; the 23-kDa zein gene from maize described by Schernthaner et al., *EMBO J.* 7: 1249, 1988; or the French bean β-phaseolin gene described by Bustos et al., *Plant Cell* 1: 839, 1989).

Plant expression vectors may also optionally include RNA processing signals, e.g, introns, which have been shown to be important for efficient RNA synthesis and accumulation (Callis et al., *Genes and Dev.* 1: 1183, 1987). The location of the RNA splice sequences can dramatically influence the level of transgene expression in plants. In view of this fact, an intron may be positioned upstream or downstream of a C-14 sterol reductase polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84: 744, 1987; An et al., *Plant Cell* 1:115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Alternatively, the green-fluorescent protein from the jellyfish *Aequorea victoria* may be used as a selectable marker (Sheen et al., *Plant J.* 8:777, 1995; Chiu et al., *Current Biology* 6: 325, 1996). Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 $\mu$g/ml (kanamycin), 20–50 $\mu$g/ml (hygromycin), or 5–10 $\mu$g/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller In: *Genetic Engineering*, vol 6, P W J Rigby, ed, London, Academic Press, 1987; and Lichtenstein, C. P., and Draper, J,. In: *DNA Cloning*, Vol II, D. M. Glover, ed, Oxford, IRI Press, 1985)), (2) the particle delivery system (see, e.g., Gordon-Kamm et al., *Plant Cell* 2: 603 (1990); or BioRad Technical Bulletin 1687, supra), (3) microinjection protocols (see, e.g., Green et al., supra), (4) polyethylene glycol (PEG) procedures (see, e.g., Draper et al., *Plant Cell Physiol.* 23: 451, 1982; or e.g., Zhang and Wu, *Theor. Appl. Genet.* 76: 835, 1988), (5) liposome-mediated DNA uptake (see, e.g., Freeman et al., *Plant Cell Physiol.* 25: 1353, 1984), (6) electroporation protocols (see, e.g., Gelvin et al., supra; Dekeyser et al., supra; Fromm et al., *Nature* 319: 791, 1986; Sheen *Plant Cell* 2: 1027, 1990; or Jang and Sheen *Plant Cell* 6: 1665, 1994), and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned C-14 sterol reductase polypeptide or an antisense construct under the control of the 35S CaMV promoter and the nopaline synthase terminator and carrying a selectable marker (for example, kanamycin resistance) is transformed into Agrobacterium. Transformation of leaf discs (for example, of tobacco leaf discs), with vector-containing Agrobacterium is carried out as described by Horsch et al. (*Science* 227: 1229, 1985). Putative transformants are selected after a few weeks (for example, 3 to 5 weeks) on plant tissue culture media containing kanamycin (e.g. 100 $\mu$g/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using C-14 sterol reductase specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant C-14 sterol reductase protein is expressed in any cell or in a transgenic plant (for example, as described above), it may be isolated, e.g., using affinity chromatography. In one example, an anti-C14 sterol reductase antibody (e.g., produced as described in Ausubel et al., supra, or by any standard technique) may be attached to a column and used to isolate the polypeptide. Lysis and fractionation of C-14 sterol reductase-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, *Laboratory Techniques In Biochemistry And Molecular Biology*, eds., Work and Burdon, Elsevier, 1980).

Polypeptides of the invention, particularly short C-14 sterol reductase protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful C-14 sterol reductase fragments or analogs.

Antibodies

C-14 sterol reductases described herein (or immunogenic fragments or analogs) may be used to raise antibodies useful in the invention; such polypeptides may be produced by recombinant or peptide synthetic techniques (see, e.g., *Solid Phase Peptide Synthesis*, 2nd ed., 1984, Pierce Chemical Co., Rockford, Ill.; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the C-14 sterol reductase polypeptides described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific C-14 sterol reductase recognition by Western blot or immunoprecipitation analysis (by the methods described in Ausubel et al., supra). Antibodies which specifically recognize C-14 sterol reductases are considered to be useful in the invention; such antibodies may be used, e.g., in an immunoassay to monitor the level of C-14 sterol reductase produced by a plant.

Use

Because the present invention provides for the genetic manipulation of a plant sterol biosynthetic pathway, this invention described is useful for a variety of agricultural and commercial purposes including, but not limited to, increasing crop yields, improving crop and ornamental quality, and reducing agricultural production costs. For example, the methods, DNA constructs, proteins, and transgenic plants described herein are useful for improving a number of fruit and vegetable characteristics including, but not limited to, texture, size, nutritional content, modification of sterol composition, disease and insect resistance, and ripening processes. In addition, genetic manipulation of plant sterol composition (for example, seed sterol composition) is useful for improving food quality and oil stability, and regulating the formation of compounds having anti-nutritional properties.

In one particular example, antisense C-14 sterol reductase sequences are useful for reducing the expression of C-14 sterol reductase expression in a transgenic plant. Such reduced expression of C-14 sterol reductase provides a means for increasing the life-span of such plants. Increased life-span extends reproductive period, delays senescence, and increases branch number for high productivity and yield. In addition, transgenic plants expressing antisense C-14 sterol reductase are useful for producing plants having reduced and more compact proportions. Such plants require less space and land requirements for their growth, and are more convenient and efficient to harvest.

Overproduction of the C-14 sterol reductase in transgenic plants is useful for enhancing the production of steroid compounds having a variety of medicinal or agricultural applications. For example, overproduction of mammalian steroid hormones in plants offers an inexpensive means for producing such hormones.

In addition, C-14 sterol reductase polypeptides disclosed herein are useful for the development of enzyme inhibitors of the sterol biosynthetic pathway.

Other Embodiments

In other embodiments, the invention includes any protein which is substantially identical to a crucifer C-14 sterol reductase polypeptide (FIG. 10; SEQ ID NO: 1); such homologs include other substantially pure naturally-occurring plant C-14 sterol reductase proteins as well as allelic variants; natural mutants; induced mutants; proteins encoded by DNA that hybridizes to the C-14 sterol reductase DNA sequence of FIGS. 14–1 to 14–6 (SEQ ID NO: 2) under high stringency conditions or, less preferably, under low stringency conditions (e.g., washing at 2×SSC at 37° C. with a probe length of at least 10–15 nucleotides), both as described herein; and proteins specifically bound by antisera directed to a C-14 sterol reductase polypeptide. The term also includes chimeric polypeptides that include a C-14 sterol reductase portion.

The invention further includes analogs of any naturally-occurring plant C-14 sterol reductase polypeptide. Analogs can differ from the naturally-occurring C-14 sterol reductase protein by amino acid sequence differences, by post-translational modifications, or by both. Analogs of the invention will generally exhibit at least 30%, more preferably 40%, and most preferably 50% or even 80–95% identity with all or part of a naturally-occurring plant C-14 sterol reductase amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring C-14 sterol reductase polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes C-14 sterol reductase polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of C-14 sterol reductase polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Furthermore, the invention includes nucleotide sequences that facilitate specific detection of a C-14 sterol reductase nucleic acid. Thus, C-14 sterol reductase sequences described herein (e.g., SEQ ID NO: 2 and 3) or portions thereof may be used as probes to hybridize to nucleotide sequences from other plants (e.g., dicots, monocots, gymnosperms, and algae) by standard hybridization techniques under conventional conditions. Sequences that hybridize to a C-14 sterol reductase coding sequence or its complement and that encode a C-14 sterol reductase are considered useful in the invention. As used herein, the term "fragment," as applied to nucleic acid sequences, means at least 5 contiguous nucleotides, preferably at least 10 contiguous nucleotides, more preferably at least 20 to 30 contiguous nucleotides, and most preferably at least 40 to 80 or more contiguous nucleotides. Fragments of C-14 sterol reductase nucleic acid sequences can be generated by methods known to those skilled in the art.

All publications and patent applications mentioned in this specification are herein incorporated by reference to the same extent as if each independent publication or patent application was specifically and individually indicated to be incorporated by reference.

Other embodiments are within the following claims.

What is claimed is:

1. A purified plant nucleic acid molecule that specifically hybridizes under highly stringent conditions to the complement of the sequence set forth in SEQ ID NO:2, wherein said highly stringent conditions comprise
   a) hybridization at 65° C. and 50% formamide,
   b) a first wash at 65° C., 2×SSC, and 1% SDS, and
   c) a second wash at 65° C. and 0.1% SDS, and 0.1×SSC, and said nucleic acid molecule encodes a protein having C-14 sterol reductase activity.

2. The purified plant nucleic acid molecule of claim 1, wherein said nucleic acid molecule comprises the sequence set forth in SEQ ID NO: 2.

3. The purified plant nucleic acid molecule of claim 1, wherein said nucleic acid molecule encodes the amino acid sequence set forth in SEQ ID NO: 1.

4. The purified plant nucleic acid molecule of claim 1, wherein said DNA is from a dicot.

5. The purified plant nucleic acid molecule of claim 4, wherein said dicot is a crucifer.

6. A vector comprising the purified plant nucleic acid molecule of claim 1.

7. The vector of claim 6, wherein said nucleic acid molecule comprises the sequence set forth in SEQ ID NO: 2.

8. The vector of claim 6, wherein said nucleic acid molecule encodes the amino acid sequence set forth in SEQ ID NO: 1.

9. The vector of claim 6, wherein said DNA is from a dicot.

10. The vector of claim 7, wherein said dicot is a crucifer.

11. A host cell comprising the purified plant nucleic acid molecule of claim 1.

12. The host cell of claim 11, wherein said nucleic acid molecule comprises the sequence set forth in SEQ ID NO: 2.

13. The host cell of claim 11, wherein said nucleic acid molecule encodes the amino acid sequence set forth in SEQ ID NO: 1.

14. The host cell of claim 11, wherein said DNA is from a dicot.

15. The host cell of claim 14, wherein said dicot is a crucifer.

16. A method of producing a C-14 sterol reductase polypeptide comprising providing a host cell transformed with the purified plant nucleic acid molecule of claim 1, said nucleic acid molecule encoding a C-14 sterol reductase polypeptide, culturing said host cell, wherein said plant nucleic acid molecule is expressed, and recovering said C-14 sterol reductase polypeptide.

17. The method of claim 16, wherein said host cell is a plant cell.

18. The method of claim 14, wherein said nucleic acid molecule comprises the sequence set forth in SEQ ID NO: 2.

19. The method of claim 14, wherein said nucleic acid molecule encodes the amino acid sequence set forth in SEQ ID NO: 1.

20. The method of claim 14, wherein said DNA, is from a dicot.

21. The method of claim 20, wherein said dicot is a crucifer.

22. A plant comprising the purified plant nucleic acid molecule of claim 1 integrated into the genome of said plant, wherein said plant nucleic acid molecule is expressed in said plant.

23. A transgenic seed from the plant of claim 22.

24. A transgenic cell from the plant of claim 22.

25. The plant of claim 22, wherein said nucleic acid molecule comprises the sequence set forth in SEQ ID NO: 2.

26. The plant of claim 22, wherein said nucleic acid molecule encodes the amino acid sequence set forth in SEQ ID NO: 1.

27. The plant of claim 22, wherein said DNA is from a dicot.

28. The plant of claim 27, wherein said dicot is a crucifer.

* * * * *

SEQUENCE LISTING

<160> NUMBER OF SEQ ID NOS: 24

<210> SEQ ID NO 1
<211> LENGTH: 368
<212> TYPE: PRT
<213> ORGANISM: Arabidopsis thaliana

<400> SEQUENCE: 1

```
Met Leu Leu Asp Met Asp Leu Gly Val Leu Leu Pro Ser Leu Gln Ser
 1               5                  10                  15

Val Tyr Val Leu Val Phe Tyr Phe Val Tyr Leu Ala Val Ala Gly Glu
                20                  25                  30

Ile Leu Pro Gly Lys Val Ile Arg Gly Val Leu Leu Ser Asp Gly Ser
            35                  40                  45

Gln Leu Arg Tyr Arg Cys Asn Gly Leu Leu Ala Leu Ile Leu Leu Val
        50                  55                  60

Ala Ile Leu Gly Ile Cys Ala Lys Leu Gly Ile Val Ser Pro Leu Val
    65                  70                  75                  80

Val Ala Asp Arg Gly Leu Glu Leu Leu Ser Ala Thr Phe Ile Phe Cys
                85                  90                  95
```

-continued

```
Val Leu Val Thr Leu Ala Leu Tyr Val Thr Gly Arg Ser Ser Ser Asn
            100                 105                 110
Lys Gly Ser Ser Leu Lys Pro His Val Ser Gly Asn Leu Val His Asp
        115                 120                 125
Trp Trp Phe Gly Ile Gln Leu Asn Pro Gln Phe Met Ser Ile Asp Leu
    130                 135                 140
Lys Phe Phe Val Arg Ala Gly Met Met Gly Trp Leu Leu Ile Asn
145                 150                 155                 160
Leu Ser Ile Leu Ala Lys Ser Val Gln Asp Gly Ser Leu Ser Gln Ser
                165                 170                 175
Met Ile Leu Tyr Gln Ile Phe Cys Ala Leu Tyr Ile Leu Asp Tyr Phe
            180                 185                 190
Val His Glu Glu Tyr Met Thr Ser Thr Trp Asp Ile Ile Ala Glu Arg
        195                 200                 205
Leu Gly Phe Met Leu Val Phe Gly Asp Leu Leu Trp Ile Pro Phe Thr
    210                 215                 220
Phe Ser Ile Gln Gly Trp Trp Leu Leu His Asn Lys Val Glu Leu Thr
225                 230                 235                 240
Val Pro Ala Ile Val Asn Cys Leu Val Phe Leu Ile Gly Tyr Met
                245                 250                 255
Val Phe Arg Gly Ala Asn Lys Gln Lys His Ile Phe Lys Lys Asn Pro
            260                 265                 270
Lys Thr Pro Ile Trp Gly Lys Pro Val Val Gly Gly Lys Leu
        275                 280                 285
Leu Val Ser Gly Tyr Trp Gly Ile Ala Arg His Cys Asn Tyr Leu Gly
    290                 295                 300
Asp Leu Met Leu Ala Leu Ser Phe Ser Leu Pro Cys Gly Ile Ser Ser
305                 310                 315                 320
Pro Val Pro Tyr Phe Tyr Pro Ile Tyr Leu Ile Leu Leu Ile Trp
                325                 330                 335
Arg Glu Arg Arg Asp Glu Val Arg Cys Ala Glu Lys Tyr Lys Glu Ile
            340                 345                 350
Trp Ala Glu Tyr Leu Arg Leu Val Pro Trp Arg Ile Leu Pro Tyr Val
        355                 360                 365

<210> SEQ ID NO 2
<211> LENGTH: 1429
<212> TYPE: DNA
<213> ORGANISM: Arabidopsis thaliana
<220> FEATURE:
<221> NAME/KEY: CDS
<222> LOCATION: (84)...(1189)
<221> NAME/KEY: variation
<222> LOCATION: (1)...(1429)
<223> OTHER INFORMATION: N can be any nucleotide.

<400> SEQUENCE: 2
ctgaaattaa acaaagcgag aaaaggcgat acaaacgatt tcgaatgctt catcttctcc     60
tttgaaaatc cttcttctgc tta atg ctg cta gat atg gat ctc ggt gtt ctt    113
                         Met Leu Leu Asp Met Asp Leu Gly Val Leu
                           1               5                  10 ctt cca tca ttg caa tct gtt tat gtg ctg gtg ttt tac ttc gtt tac      161
Leu Pro Ser Leu Gln Ser Val Tyr Val Leu Val Phe Tyr Phe Val Tyr
             15                  20                  25 ttg gcc gtt gcc gga gaa att ctc ccc ggg aaa gtt att cgc ggc gtc      209
Leu Ala Val Ala Gly Glu Ile Leu Pro Gly Lys Val Ile Arg Gly Val
         30                  35                  40
```

```
ctt tta tca gat ggc tct caa ctt cgt tac cga tgc aat ggt cta ttg        257
Leu Leu Ser Asp Gly Ser Gln Leu Arg Tyr Arg Cys Asn Gly Leu Leu
            45                  50                  55 gca cta ata ttg ttg gta gct att ttg gga atc tgt gca aaa ctt ggc        305
Ala Leu Ile Leu Leu Val Ala Ile Leu Gly Ile Cys Ala Lys Leu Gly
        60                  65                  70 att gta tca cct ctt gtg gtt gcg gat aga gga ctt gag tta ctc tca        353
Ile Val Ser Pro Leu Val Val Ala Asp Arg Gly Leu Glu Leu Leu Ser
75                  80                  85                  90 gct act ttt att ttc tgt gtt ttg gtg aca tta gca ttg tat gtt act        401
Ala Thr Phe Ile Phe Cys Val Leu Val Thr Leu Ala Leu Tyr Val Thr
                95                 100                 105 ggg cga agt tcc tcg aat aag ggt tct tcc cta aag cct cat gtc tca        449
Gly Arg Ser Ser Ser Asn Lys Gly Ser Ser Leu Lys Pro His Val Ser
        110                 115                 120 gga aat ctt gta cat gac tgg tgg ttt gga ata cag ctg aat cct cag        497
Gly Asn Leu Val His Asp Trp Trp Phe Gly Ile Gln Leu Asn Pro Gln
        125                 130                 135 ttt atg agc att gat ctc aag ttt ttc ttt gtc aga gcc ggg atg atg        545
Phe Met Ser Ile Asp Leu Lys Phe Phe Phe Val Arg Ala Gly Met Met
        140                 145                 150 gga tgg ctg ctt atc aat ctc tct att ctg gca aaa agt gtg cag gat        593
Gly Trp Leu Leu Ile Asn Leu Ser Ile Leu Ala Lys Ser Val Gln Asp
155                 160                 165                 170 ggt tcc ttg agt cag tcg atg att ctt tac cag atc ttc tgt gcg tta        641
Gly Ser Leu Ser Gln Ser Met Ile Leu Tyr Gln Ile Phe Cys Ala Leu
                175                 180                 185 tat ata ttg gac tac ttt gtt cat gaa gaa tac atg acc tct acg tgg        689
Tyr Ile Leu Asp Tyr Phe Val His Glu Glu Tyr Met Thr Ser Thr Trp
        190                 195                 200 gac ata att gca gag aga cta ggc ttc atg cta gtg ttt gga gat ctc        737
Asp Ile Ile Ala Glu Arg Leu Gly Phe Met Leu Val Phe Gly Asp Leu
        205                 210                 215 ctg tgg att cct ttc act ttt agc att cag ggc tgg tgg ctt ttg cac        785
Leu Trp Ile Pro Phe Thr Phe Ser Ile Gln Gly Trp Trp Leu Leu His
        220                 225                 230 aac aaa gta gaa cta aca gtt cct gcg att gta gtc aat tgc ctt gtc        833
Asn Lys Val Glu Leu Thr Val Pro Ala Ile Val Val Asn Cys Leu Val
235                 240                 245                 250 ttc ttg ata ggg tac atg gtt ttt cga gga gct aac aaa caa aaa cat        881
Phe Leu Ile Gly Tyr Met Val Phe Arg Gly Ala Asn Lys Gln Lys His
                255                 260                 265 atc ttt aag aag aac cca aaa aca cca ata tgg ggc aag cct cca gtg        929
Ile Phe Lys Lys Asn Pro Lys Thr Pro Ile Trp Gly Lys Pro Pro Val
        270                 275                 280 gta gtt ggt gga aag tta ctg gtt tca ggc tat tgg gga att gca agg        977
Val Val Gly Gly Lys Leu Leu Val Ser Gly Tyr Trp Gly Ile Ala Arg
        285                 290                 295 cac tgt aat tac ctt ggc gac ttg atg ctt gct ctg tcc ttc agt ttg       1025
His Cys Asn Tyr Leu Gly Asp Leu Met Leu Ala Leu Ser Phe Ser Leu
        300                 305                 310 cca tgt gga ata agt tct ccg gtt cca tat ttc tac ccg ata tac ctt       1073
Pro Cys Gly Ile Ser Ser Pro Val Pro Tyr Phe Tyr Pro Ile Tyr Leu
315                 320                 325                 330 ctg ata cta ttg ata tgg aga gaa cga aga gac gag gtt cga tgt gca       1121
Leu Ile Leu Leu Ile Trp Arg Glu Arg Arg Asp Glu Val Arg Cys Ala
                335                 340                 345 gag aag tac aag gag ata tgg gca gag tat ctt aga ctt gtc ccc tgg       1169
Glu Lys Tyr Lys Glu Ile Trp Ala Glu Tyr Leu Arg Leu Val Pro Trp
```

-continued

```
                        350                 355                 360
aga ata ctt cct tat gtt ta ttagatgtgc caagagccaa gtcatgaatc             1219
Arg Ile Leu Pro Tyr Val
            365 ctttcagatt cacctcttgt tgtcttattt tttccataat cttgttttat tttagcaatg       1279 ctcgaattga aactttgtag tacactttg aaaaataact tcagtcctta aaaaaaaaa         1339 aaacctaant tactcccnct gggcggccgc tggttttata tttgttgtaa aaattaaana       1399 attactncct tgangatctg taaaaaaaaa                                        1429
```

<210> SEQ ID NO 3
<211> LENGTH: 6587
<212> TYPE: DNA
<213> ORGANISM: Arabidopsis thaliana
<220> FEATURE:
<221> NAME/KEY: variation
<222> LOCATION: (1)...(6587)
<223> OTHER INFORMATION: N can be any nucleotide.

<400> SEQUENCE: 3

```
tnttgaaggn tnaagaaaaa ntanggtaag ctgggnagga caaganttct tgtnaccaca         60
acacaacaac gccatgaacc natcggtttc ttntgtttng agatcacctt tcttgagttg        120
gtggtttctg agntcaagnt ccttgttgac tcagtgaagt ccagatgcag cntcaaaact        180
tttgtcctgt agacntagca agagtaacag caccaaccaa atcgctatcc gatgtaatca        240
aaaccttatc acnttcatcg tcctcatata taatctgagg ccgttgttcc acattgttat        300
tgtcgctgcc aattctttgc atcacaatac ccatcagctn ttcgaggttt tcagctccag        360
aagtaaaccg atgtacacgg cccttaaggt cttcaaattt gaacgaaaac gaattcccta        420
gtcctagaga tgggtaagaa ctgagcttcc ctatatctga atgatgcatc attgccgaca        480
tttcactttg agtgtcagaa tcatcaggtg gctctaacgc aagagctgaa tcccaaaatt        540
tctgcatcat cgtgtttgcc atatcattta cagctccaga actgttctcc accattgaaa        600
tagctgcgtg agtaatctga agaacgtcta cacaagctgc agctgatcca tctttatcta        660
taattggaag atgtagaaac tttccatcat gcattgtatg caatgcatcc agaatcgttg        720
tctctagcga tgcacattca ggattcggtg tcattacctt ctcgacaaga gtcaattcag        780
gagataaatt ttgtgccacc actcgcatca gaatgtcctt gaagtcaag attccactga         840
ttttgttccc ccgtggaaat gattacagag ttaacccgca aatccctcat ccttttcgca        900
gcaactgaaa caggatctga tggtgctaca agtgcaacct tcgatgtctg taataatcgt        960
gacaaggcgg gttaaacatt mtmtccttca aggtttcaat gaaagcatac ggtgcagaat       1020
atccgcttcc ccattgtttn tccacacctt ccactgcagc agctaaagca ctaccttgct       1080
ctgcagtttc tccatcctag aaatagcatc atacaaacac tttgtaatat ccaacaaagc       1140
aatgacttca ccattctcca caacaggcaa gtgtctaaac ttcccttgaa ccatcttctg       1200
aagagcctca agcgccaacg aatcagaagt aacaaaaata ggattcctag tcataacctt       1260
agagaccaaa gtttgatccg gtctcaaccc ttcagcaatc actcttgtag ctacatcttt       1320
atcagtaaca atcccggaaa gaagcgcact tgaatcagtc aacaaacaag catcaacacg       1380
cctagcagcc attnttcgac aagcatcgaa acagtagtt ccttcnagga atagtaagag       1440
ctttcgataa cctaagcttc ttcgctgtct ctctccatta gaaggagctt gagattgagg       1500
ttgaggagga ggtgaattgg gttttgaggt gttcccanta acacttccat tctctgattg       1560
tactggtttc ttagaaggtg gtggtcctcn ccgtacagta gaattgcttc tcctccctga       1620
```

```
tgttgaagaa ggacccgtcg cttgagtact catattcggt caatctaggg tttacttaga    1680
tcctaaatcc gtcanaaatg attcctttag atatcaaact cgtctctgca aatgaaaaat    1740 tcaacctttaa attcacaaac tattgaaatt tcatctaaag cacgaatctg aataaaaccc    1800
aattcacaat aaagacgatt tgctctgaga atacgatgca acatacacga aaaggattcg    1860
aatttaacgg acgagggaaa tgaaacaact tgaaacccta aggatttgag cagaagttat    1920
gtgggaagat tgggnattta gggtttacct tcttctttct tcntcaaggt ctctctctcg    1980
agcactttcg ttncccaaa aacnaacggc tcttaacaat tgagttaanc canttatcga    2040
gttttcattg gntgttcctg tttccgcgtg tgtggtggnt cnccacctcc tttcttataa    2100
tcnacgacta aaaatgttaa anataanact aanatttctt tctanaaaaa tcgtaaaanc    2160
caaatgtttt ttttttttctg ataaatgtct ataaatcacc ctttcttttt aaataatgaa    2220
atttgatgac atttatctct tgtatctagn agagttaatg ctaacataa anaccaaaaa    2280 aaattaattc naataaatat gatttgtgtg ggttacatgg aaaaattgtc aaataataaa    2340
ncaaaaaaaa attgtataga tgcagtgcaa gttgtttctg gtcaacttgc cgtcgagcct    2400
cacaactgtt tgttacaagt ggactcgcat gtaattccct cttttaataa cttaccagtt    2460
acaccatcca acatgtgatt tgacagaaaa atattttagt gaaatgtgat cggtgcagat    2520
ttttctatgt acgtttaagc ctttaaggta gacgtttaat ccnaaaatat ccctgaataa    2580
caacaccgat taatgaaacc aagtagatac ctcctccgtt tggatggctc aaatgcaacc    2640
atgatgcaag cttttgcgat tgacccaaag tgagagaact agatcgagat ggattattcg    2700
gaaccattac cgcacccttta taatggca gcatcttaat agtaaacaaa agctttagcc    2760
ttaggtttta gcttccttca ctctttgcat acattgtgaa tctgcggttt tagatggacc    2820
atagtggaaa aaggctttca tcaataactc gtggacttga tcaatggtag aaaaganaat    2880
acatagtatg gaaaactaga tatttgatat atttggttca aactcttatc cggtgttgag    2940
gtgatataca catgaagaca taacaatcgc atagccgaga aactagtatt cattaacctt    3000
tttctctaaa gagattgtcc tatcaatcta aattttagat gttaaaaaaa aatggtaagg    3060
ttaaacaggc cgctaggttg gtttttacgat gatgtaaaaa gtagccatct taaaataaca    3120
gtcgtttgcg agactggcca ggccatccca tgggccatag gctcgctcaa gttgtgcttg    3180
gcagaattta gtaacttggg gttttgttat caacaatcaa tagtttaagg ctttacctgc    3240
aagaaatgaa gagtttaagg gttctttttg gtattcccga ttcacacaag tgagctagct    3300
catcagagtc cacgagcttc ccactaaaaa attgaaaatt gttgcttctg tcatctgaaa    3360
ttaaacaaag cgagaaaagg cgatacaaac gatttcgaat gcttcatctt ctcctttgaa    3420
aatccttctt ctgcttaatg ctgctagata tggatctcgg tgttcttctt ccatcattgc    3480
aatctgtgag ctgtctcttt agcttttgac tgttgcaatt gttattgtga aattttttgtt    3540 cgcttttgga tcagcttttg ttaaattcgt tccgagattt taggtttatg tgctggtgtt    3600
ttacttcgtt tacttgggnc gntggcggag aaattctccc cgggaaagtt attcgcggcg    3660 tcctttttatc agatggctct caacttcgtt accgatgcaa tggtatattt gatttgattt    3720
actctctcta caattcctga gagtctgtga gctcgaaagt tcatttccat tagttttggtt    3780 aattcaatttt caggtctatt ggcactaata ttgttggtag ctatttnggg aatctgtgca    3840
aaacttggca ttgtatcacc tcttgtaagt gtagttacaa gatttcgatt gtatttctat    3900
gaatccgaat gctatatgct atatgaatcc gattgcaatt gctttctcac actcattcca    3960
```

-continued

```
ctgagatgtt tggtaggtgg ttgcggatag aggacttgag ttactctcag ctacttnnat    4020
ttcttgtgtt tggggaagat gatcaatcct tagtccggng tcttggattt tagntgngtt    4080
accatcagat tngctttggg tggtgtgatt tgtaatctcc atgatatctc ttaatattct    4140
caggtgacat tagcattgta tgttactggg cgaagttcct cgaataaggg ttcttcccta    4200
aagcctcatg tctcaggaaa tcttgtacat gactggtact aacataatac aattgtagat    4260
ctgatacttt cttgttacac aaaatgttgt taaaagttat atattttgac tcctgcaaga    4320
gcaaaactaa gaaataatct ggtactatat agagtttgaa acactgaatt ggacaagatg    4380
attctataga acttcgtaga gtgttgagta atttctccta gaacggttgt agcttcctct    4440
tttttccttt taaccgcagt gactttagct tttggaactt ttctactgaa actagaagtt    4500
ctggttttgt ctttcactta tctcttccaa acaactgctt caattttttc tcatattgtt    4560
tgtttcatgt gataggtggt ttggaataca gctgaatcct cagtttatga gcattgatct    4620
caagtaatcc attttctgt tttttcttct atttgtcagc caaggctaca tcattgcttc    4680
agtttgttcc gtactcaatc gagtggcagt ttaataatgt aatcagcagt tatgcatggt    4740
tatgatgaat gggagttatt ccttgtgtag gttttctctt gtcagagccg ggatgatggg    4800
atggctgctt atcaatctct ctattctggc aaaaagtgtg caggatggtt ccttgagtca    4860
gtcgatgatc tttaccagat cttctgtgcg gtaaatttgg tttttactta caaatcttgc    4920
ttcttgaant ctgatcatct gtgttttgtt agttttgatt agttttataa ttgcagttat    4980
atatattgga tactttgttc atgaagaata catgacctct acgtaagttc atggcgtgtt    5040
aaggaaacac atttgtctta ccaaaaaatg accatttgca ttattacatc tactttgatt    5100
ttactctttt caggtgggac ataattgcag agagactagg cttcatgcta gtgtttggag    5160
atctcctgtg gattcctttc acttttagca ttcaggcatg taactgtgag cctgaacaca    5220
aacaagatat taatttatct tattgacagt atccttcttgg catgttacag ttattctcgg    5280
aaacaatatt gttctagaat gcttgatcac tctgtgactg aattgtcttc tctctggtac    5340
agggctggtg gcttttgcac aacaaagtag aactaacaat tcctgcgatt gtagtcaatt    5400
gccttgtctt cttgatagg taagttctga acatggggt tattttccat tcttacatat    5460
ctacactaag aaacccacta tttcttcttt ggcaggtaca tggttttcg aggagctaac    5520 aaacaaaaac atatctttaa gaagaaccca aaaacaccaa tatgggcaa gcctccagtg    5580 gtagttggtg gaaagttact ggtttcaggc tattggtatg ttatatttat cttctcttgt    5640
ttctttgctt ggtttcgcca tctctgtgtt tgattgttca tcatgctggg aataaagagt    5700
tgaaagttcc gcaatgacac atttccgata acttaggtgc tgttttgtat atatgacagg    5760
ggaattgcaa ggcactgtaa ttaccttggc gacttgatgc ttgctctgtc cttcagtttg    5820
ccatgtggaa taaggtactc ctnctgcttg agttcactta cagctaccaa aatcatgtag    5880
aaactaatac caatatcnaa acgttcgaag ttgatttggc tgacttaaag atattgatct    5940
ctaaccatca tttgaaaagt ctaaagcttt caagttcatt tcccaaagct gtttttatga    6000
tatttcgtct ngtgtattct cagttctccg gttccatatt tctacccgat atacctgctg    6060
atactattga tatggagaga acgaagagac gaagttcgat gtgcagagaa gtacnaggag    6120
atatgggcag agtatcttag acttgtcccc tggagaatac ttccttatgt ttattagatg    6180
tgccaagagc caattcatga atcctttcag attcatcctc ttgtgtctta ttttttcatt    6240
aaatgtgacn tgaaatgatc ccattatngc ctnttatcaa tgcttgattg aaactttgta    6300
gtacacgttt gagaattact tcagtccttg ttattatttt agcatggata tcaacatttt    6360
```

```
cggatttatt tntngggtta ttttaaaacc nnagattacc naanaaaacc attgtttgan      6420
gtangataat atggactttt tactgaaaaa aaatnctant agggggaacaa atngaagttg      6480 aatatggctg aatntttta tgganaaaat ggaaacttt cccactttga aatgacaatn        6540
caagtttggt ggacnactta atcactggaa acgttaatgg ccaaccn                   6587
```

<210> SEQ ID NO 4
<211> LENGTH: 438
<212> TYPE: PRT
<213> ORGANISM: Saccharomyces cerevisiae

<400> SEQUENCE: 4

```
Met Val Ser Ala Leu Asn Pro Arg Thr Thr Glu Phe Glu Phe Gly Gly
  1               5                  10                  15

Leu Ile Gly Ala Leu Gly Ile Ser Ile Gly Leu Pro Val Phe Thr Ile
             20                  25                  30

Ile Leu Asn Gln Met Ile Arg Pro Asp Tyr Phe Ile Lys Gly Phe Phe
         35                  40                  45

Gln Asn Phe Asp Ile Val Glu Leu Trp Asn Gly Ile Lys Pro Leu Arg
     50                  55                  60

Tyr Tyr Leu Gly Asn Arg Glu Leu Trp Thr Val Tyr Cys Leu Trp Tyr
 65                  70                  75                  80

Gly Ile Leu Ala Val Leu Asp Val Ile Leu Pro Gly Arg Val Met Lys
                 85                  90                  95

Gly Val Gln Leu Arg Asp Gly Ser Lys Leu Ser Tyr Lys Ile Asn Gly
            100                 105                 110

Ile Ala Met Ser Thr Thr Leu Val Leu Val Leu Ala Ile Arg Trp Lys
        115                 120                 125

Leu Thr Asp Gly Gln Leu Pro Glu Leu Gln Tyr Leu Tyr Glu Asn His
    130                 135                 140

Val Ser Leu Cys Ile Ile Ser Ile Leu Phe Ser Phe Phe Leu Ala Thr
145                 150                 155                 160

Tyr Cys Tyr Val Ala Ser Phe Ile Pro Leu Ile Phe Lys Lys Asn Gly
                165                 170                 175

Asn Gly Lys Arg Glu Lys Ile Leu Ala Leu Gly Gly Asn Ser Gly Asn
            180                 185                 190

Ile Ile Tyr Asp Trp Phe Ile Gly Arg Glu Leu Asn Pro Arg Leu Gly
        195                 200                 205

Pro Leu Asp Ile Lys Met Phe Ser Glu Leu Arg Pro Gly Met Leu Leu
    210                 215                 220

Trp Leu Leu Ile Asn Leu Ser Cys Leu His His His Tyr Leu Lys Thr
225                 230                 235                 240

Gly Lys Ile Asn Asp Ala Leu Val Leu Val Asn Phe Leu Gln Gly Phe
                245                 250                 255

Tyr Ile Phe Asp Gly Val Leu Asn Glu Glu Gly Val Leu Thr Met Met
            260                 265                 270

Asp Ile Thr Thr Asp Gly Phe Gly Phe Met Leu Ala Phe Gly Asp Leu
        275                 280                 285

Ser Leu Val Pro Phe Thr Tyr Ser Leu Gln Ala Arg Tyr Leu Ser Val
    290                 295                 300

Ser Pro Val Glu Leu Gly Trp Val Lys Val Gly Ile Leu Ala Ile
305                 310                 315                 320

Met Phe Leu Gly Phe His Ile Phe His Ser Ala Asn Lys Gln Lys Ser
                325                 330                 335
```

```
Glu Phe Arg Gln Gly Lys Leu Glu Asn Leu Lys Ser Ile Gln Thr Lys
            340                 345                 350

Arg Gly Thr Lys Leu Leu Cys Asp Gly Trp Ala Lys Ser Gln His
            355                 360                 365

Ile Asn Tyr Phe Gly Asp Trp Leu Ile Ser Leu Ser Trp Cys Leu Ala
            370                 375                 380

Thr Trp Phe Gln Thr Pro Leu Thr Tyr Tyr Ser Leu Tyr Phe Ala
385                 390                 395                 400

Thr Leu Leu His Arg Gln Gln Arg Asp Glu His Lys Cys Arg Leu
            405                 410                 415

Lys Tyr Gly Glu Asn Trp Glu Glu Tyr Glu Arg Lys Val Pro Tyr Lys
            420                 425                 430

Ile Ile Pro Tyr Val Tyr
            435

<210> SEQ ID NO 5
<211> LENGTH: 424
<212> TYPE: PRT
<213> ORGANISM: Schizosaccharomyces pombe

<400> SEQUENCE: 5

Met Ala Lys Gly Ala Val Lys Lys Glu Lys Phe Glu Tyr Glu Phe Phe
1               5                   10                  15

Gly Pro Ile Gly Ala Leu Gly Val Thr Val Leu Thr Thr Val Val Ser
            20                  25                  30

Phe Gly Ser Phe Tyr Ile Cys Asn Glu Glu Gly Cys Pro Ala Lys Phe
            35                  40                  45

Ser Lys Ile Ser His Ile Phe Lys Lys Thr Pro Leu Phe Asp Gln Lys
        50                  55                  60

Ser Leu Ile Leu Tyr Leu Leu Trp Phe Ser Thr Leu Thr Leu Leu Trp
65                  70                  75                  80

Lys Cys Thr Asn Gly Lys Trp Ala Lys Gly Thr Pro Ile Asp Asp Lys
            85                  90                  95

Gly Thr Arg Leu Leu Tyr Lys Ile Asn Gly Phe Asn Ser Ala Cys Leu
            100                 105                 110

Ile Leu Gly Val Val Cys Thr Ser Ile Tyr Leu Leu Gly Ala Ser Cys
            115                 120                 125

Met Glu Phe Ile Trp Asp Asn Phe Leu Gln Leu Met Phe Ala Ala Tyr
            130                 135                 140

Val Phe Ser Val Val Leu Cys Thr Phe Cys Tyr Val Gln Ser Phe Phe
145                 150                 155                 160

Gly Lys Gln Gln Leu Ala Lys Gly Gly Thr Ser Gly Asn Ile Leu Phe
            165                 170                 175

Asp Trp Phe Ile Gly Arg Ser Leu Asn Pro Arg Ile Gly Asn Phe Asp
            180                 185                 190

Ile Lys Cys Phe Cys Glu Leu Arg Pro Gly Leu Ile Leu Trp Val Val
            195                 200                 205

Phe Asp Ile Ala Phe Ala Cys His Gln Tyr Leu Val Leu Gly Gly Arg
            210                 215                 220

Ile Thr Asp Ser Met Val Leu Val Ile Phe His Thr Trp Tyr Val
225                 230                 235                 240

Leu Asp Ser Leu Ile Asn Glu Ser Ala Val Leu Thr Thr Met Asp Ile
            245                 250                 255

Thr Thr Asp Gly Phe Gly Tyr Met Leu Ser Phe Gly Asp Leu Val Trp
```

-continued

```
                260                 265                 270
Val Pro Phe Leu Tyr Ser Leu Gln Ala Arg Tyr Leu Ala Phe His Pro
            275                 280                 285
Val Asp Leu Gly Leu Val Lys Thr Leu Ala Ile Leu Cys Leu Gln Phe
290                 295                 300
Leu Gly Tyr Tyr Ile Phe Arg Gly Ala Asn Gly Gln Lys Asn Arg Phe
305                 310                 315                 320
Arg Ser Asn Pro Asn Asp Pro Lys Leu Lys His Leu Lys Phe Ile Gln
            325                 330                 335
Thr Lys Arg Gly Thr Lys Leu Leu Thr Ser Gly Trp Trp Gly Met Ala
            340                 345                 350
Arg His Ile Asn Tyr Phe Gly Asp Trp Ile Met Ala Trp Ala Trp Cys
            355                 360                 365
Leu Pro Ala Gly Phe Gly Ser Pro Ile Pro Tyr Phe Tyr Val Ala Tyr
            370                 375                 380
Phe Gly Val Leu Leu Val His Arg Asn Ala Arg Asp Asp His Lys Cys
385                 390                 395                 400
Arg Val Lys Tyr Gly Glu Asp Trp Glu Lys Tyr Cys Lys Ala Val Lys
            405                 410                 415
Tyr Arg Ile Ile Pro Tyr Val Tyr
            420

<210> SEQ ID NO 6
<211> LENGTH: 453
<212> TYPE: PRT
<213> ORGANISM: Schizosaccharomyces pombe

<400> SEQUENCE: 6

Met Lys Ser Thr Val Lys Lys Ser Ala Pro Arg Glu Phe Gly Gly Ala
1               5                   10                  15
Lys Gly Ala Leu Ala Ile Met Thr Gly Phe Pro Cys Leu Met Tyr Tyr
            20                  25                  30
Leu Trp Ala Cys Ser Lys Phe Asn Asp Ser Gln Phe Ile Lys Pro Glu
        35                  40                  45
Ser Phe Thr Ile Ala Gly Phe Gln Asn Phe Phe Arg Thr Leu Gly His
    50                  55                  60
Tyr Ile Tyr Val Gly Ala Tyr Pro Thr Arg Tyr Ala Phe Leu Val Phe
65                  70                  75                  80
Trp Ser Phe Cys Ile Val Gln Ala Val Met Tyr Leu Thr Leu Pro Gly
                85                  90                  95
Val Arg Thr Gln Gly Leu Pro Leu Lys His Arg Asn Asn Glu Arg Leu
            100                 105                 110
Pro Tyr Leu Cys Asn Ala Ile Trp Ser Phe Tyr Thr Thr Ile Val Ile
        115                 120                 125
Leu Ala Val Leu His Val Thr His Val Phe Pro Ile Thr Thr Phe Ile
    130                 135                 140
Asp Met Phe Gly Pro Leu Met Ser Val Ala Ile Ile Thr Ala Phe Val
145                 150                 155                 160
Cys Thr Phe Val Leu Tyr Thr Gly Thr Leu Leu Phe Gly Asp Arg Leu
                165                 170                 175
Phe Asp Lys Pro His Arg Leu Ser Gly Asn Pro Ile Tyr Asp Ala Phe
            180                 185                 190
Met Gly Ala Cys Leu Asn Pro Arg Leu Gly Lys Leu Leu Asp Phe Lys
        195                 200                 205
```

-continued

```
Met Phe Glu Val Arg Ile Pro Trp Phe Ile Leu Phe Ile Ser
    210                 215                 220

Val Gly Ala Ala Val Arg Gln Tyr Glu Thr Tyr Gly Thr Val Ser Pro
225                 230                 235                 240

Gln Val Leu Phe Val Cys Leu Gly His Tyr Leu Tyr Ala Asn Ala Cys
                245                 250                 255

Ser Lys Gly Glu Gln Leu Ile Val Pro Thr Trp Asp Met Ala Tyr Glu
            260                 265                 270

Lys Phe Gly Phe Met Leu Ile Phe Trp Asn Met Ala Gly Val Pro Phe
        275                 280                 285

Thr Tyr Ser His Cys Thr Leu Tyr Leu Phe Ser His Asp Pro Ser Val
    290                 295                 300

Tyr Asn Trp Ser Thr Gln Tyr Thr Thr Gly Ile Tyr Val Leu Leu Leu
305                 310                 315                 320

Cys Cys Tyr Tyr Ile Phe Asp Thr Cys Asn Gly Gln Lys Asn His Phe
                325                 330                 335

Arg Asn Gln Ile Tyr Gly Thr Glu Val His Arg Lys Thr Phe Pro Gln
            340                 345                 350

Leu Pro Trp Leu Ile Ile Lys Asn Pro Thr Phe Ile Arg Cys Ala Asn
        355                 360                 365

Gly Gly Thr Leu Leu Thr Ser Gly Trp Tyr Arg Tyr Ala Arg Lys Ile
    370                 375                 380

His Tyr Thr Ala Asp Phe Phe Gln Ser Leu Ser Trp Ala Leu Ile Thr
385                 390                 395                 400

Gly Phe Gln Ser Pro Leu Pro Tyr Phe Tyr Pro Cys Phe Phe Val
                405                 410                 415

Val Leu Val His Arg Val Ser Arg Asp Ile Lys Lys Cys Lys Ala Lys
            420                 425                 430

Tyr Gly Ala Asp Phe Asp Glu Tyr Cys Arg Ile Cys Pro Tyr Leu Phe
        435                 440                 445

Ile Pro Tyr Ile Phe
    450

<210> SEQ ID NO 7
<211> LENGTH: 473
<212> TYPE: PRT
<213> ORGANISM: Saccharomyces cerevisiae

<400> SEQUENCE: 7

Met Ala Lys Asp Asn Ser Glu Lys Leu Gln Val Gln Gly Glu Glu Lys
1               5                   10                  15

Lys Ser Lys Gln Pro Val Asn Phe Leu Pro Gln Gly Lys Trp Leu Lys
            20                  25                  30

Pro Asn Glu Ile Glu Tyr Glu Phe Gly Gly Thr Thr Gly Val Ile Gly
        35                  40                  45

Met Leu Ile Gly Phe Pro Leu Leu Met Tyr Tyr Met Trp Ile Cys Ala
    50                  55                  60

Glu Phe Tyr His Gly Lys Val Ala Leu Pro Lys Ala Gly Glu Ser Trp
65                  70                  75                  80

Met His Phe Ile Lys His Leu Tyr Gln Leu Val Leu Glu Asn Gly Ile
                85                  90                  95

Pro Glu Lys Tyr Asp Trp Thr Ile Phe Leu Thr Phe Trp Val Phe Gln
            100                 105                 110

Ile Ile Phe Tyr Tyr Thr Leu Pro Gly Ile Trp Thr Lys Gly Gln Pro
        115                 120                 125
```

Leu Ser His Leu Lys Gly Lys Gln Leu Pro Tyr Phe Cys Asn Ala Met
    130                 135                 140

Trp Thr Leu Tyr Val Thr Thr Leu Val Leu Val Leu His Phe Thr
145                 150                 155                 160

Asn Leu Phe Arg Leu Tyr Val Ile Ile Asp Arg Phe Gly Arg Ile Met
                165                 170                 175

Thr Cys Ala Ile Ile Ser Gly Phe Ala Phe Ser Ile Ile Leu Tyr Leu
                180                 185                 190

Trp Thr Leu Phe Ile Ser His Asp Tyr His Arg Met Thr Gly Asn His
            195                 200                 205

Leu Tyr Asp Phe Phe Met Gly Ala Pro Leu Asn Pro Arg Trp Gly Ile
    210                 215                 220

Leu Asp Leu Lys Met Phe Phe Glu Val Arg Leu Pro Trp Phe Thr Leu
225                 230                 235                 240

Tyr Phe Ile Thr Leu Gly Ala Cys Leu Lys Gln Trp Glu Thr Tyr Gly
                245                 250                 255

Tyr Val Thr Pro Gln Leu Gly Val Val Met Leu Ala His Trp Leu Tyr
                260                 265                 270

Ala Asn Ala Cys Ala Lys Gly Glu Glu Leu Ile Val Pro Thr Trp Asp
            275                 280                 285

Met Ala Tyr Glu Lys Phe Gly Phe Met Leu Ile Phe Trp Asn Ile Ala
    290                 295                 300

Gly Val Pro Tyr Thr Tyr Cys His Cys Thr Leu Tyr Leu Tyr Tyr His
305                 310                 315                 320

Asp Pro Ser Glu Tyr His Trp Ser Thr Leu Tyr Asn Val Ser Leu Tyr
                325                 330                 335

Val Val Leu Leu Cys Ala Tyr Tyr Phe Phe Asp Thr Ala Asn Ala Gln
                340                 345                 350

Lys Asn Ala Phe Arg Lys Gln Met Ser Gly Asp Lys Thr Val Arg Lys
            355                 360                 365

Thr Phe Pro Phe Leu Pro Tyr Gln Ile Leu Lys Asn Pro Lys Tyr Met
    370                 375                 380

Val Thr Ser Asn Gly Ser Tyr Leu Leu Ile Asp Gly Trp Tyr Thr Leu
385                 390                 395                 400

Ala Arg Lys Ile His Tyr Thr Ala Asp Trp Thr Gln Ser Leu Val Trp
                405                 410                 415

Ala Leu Ser Cys Gly Phe Asn Ser Val Phe Pro Trp Phe Phe Pro Val
                420                 425                 430

Phe Phe Leu Val Val Leu Ile His Arg Ala Phe Arg Asp Gln Ala Lys
            435                 440                 445

Cys Lys Arg Lys Tyr Gly Lys Asp Trp Asp Glu Tyr Cys Lys His Cys
    450                 455                 460

Pro Tyr Val Phe Ile Pro Tyr Val Phe
465                 470

<210> SEQ ID NO 8
<211> LENGTH: 637
<212> TYPE: PRT
<213> ORGANISM: Gallus domesticus

<400> SEQUENCE: 8

Met Pro Asn Arg Lys Tyr Ala Asp Gly Glu Val Val Met Gly Arg Trp
1               5                   10                  15

Pro Gly Ser Val Leu Tyr Tyr Glu Val Gln Val Thr Ser Tyr Asp Asp

|     |     |     | 20  |     |     | 25  |     |     | 30  |     |     |
|-----|-----|-----|-----|-----|-----|-----|-----|-----|-----|-----|-----|
| Ala | Ser | His | Leu | Tyr | Thr | Val | Lys | Tyr | Lys | Asp | Gly | Thr | Glu | Leu | Ala |
|     |     | 35  |     |     |     | 40  |     |     |     | 45  |     |

Ala Ser His Leu Tyr Thr Val Lys Tyr Lys Asp Gly Thr Glu Leu Ala
                35                  40                  45

Leu Lys Glu Ser Asp Ile Arg Leu Gln Ser Ser Phe Lys Gln Arg Lys
         50                  55                  60

Ser Gln Ser Ser Ser Ser Pro Ser Arg Arg Ser Arg Ser Arg Ser
65                   70                  75                  80

Arg Ser Arg Ser Pro Gly Arg Pro Ala Lys Gly Arg Arg Ser Ser
                 85                  90                  95

Ser His Ser Arg Glu His Lys Glu Asp Lys Lys Ile Ile Gln Glu
             100                 105                 110

Thr Ser Leu Ala Pro Pro Lys Pro Ser Glu Asn Asn Thr Arg Arg Tyr
             115                 120                 125

Asn Gly Glu Pro Asp Ser Thr Glu Arg Asn Asp Thr Ser Ser Lys Leu
         130                 135                 140

Leu Glu Gln Gln Lys Leu Lys Pro Asp Val Glu Met Glu Arg Val Leu
145                 150                 155                 160

Asp Gln Tyr Ser Leu Arg Ser Arg Arg Glu Glu Lys Lys Lys Glu Glu
                 165                 170                 175

Ile Tyr Ala Glu Lys Lys Ile Phe Glu Ala Ile Lys Thr Pro Glu Lys
             180                 185                 190

Pro Ser Ser Lys Thr Lys Glu Leu Glu Phe Gly Gly Arg Phe Gly Thr
             195                 200                 205

Phe Met Leu Met Phe Phe Leu Pro Ala Thr Val Leu Tyr Leu Val Leu
         210                 215                 220

Met Cys Lys Gln Asp Asp Pro Ser Leu Met Asn Phe Pro Pro Leu Pro
225                 230                 235                 240

Ala Leu Glu Ser Leu Trp Glu Thr Lys Val Phe Gly Val Phe Leu Leu
             245                 250                 255

Trp Phe Phe Phe Gln Ala Leu Phe Tyr Leu Leu Pro Ile Gly Lys Val
                 260                 265                 270

Val Glu Gly Leu Pro Leu Ser Asn Pro Arg Lys Leu Gln Tyr Arg Ile
             275                 280                 285

Asn Gly Phe Tyr Ala Phe Leu Leu Thr Ala Ala Ile Gly Thr Leu
         290                 295                 300

Leu Tyr Phe Gln Phe Glu Leu His Tyr Leu Tyr Asp His Phe Val Gln
305                 310                 315                 320

Phe Ala Val Ser Ala Ala Phe Ser Met Ala Leu Ser Ile Tyr Leu
                 325                 330                 335

Tyr Ile Arg Ser Leu Lys Ala Pro Glu Glu Asp Leu Ala Pro Gly Gly
             340                 345                 350

Asn Ser Gly Tyr Leu Val Tyr Asp Phe Phe Thr Gly His Glu Leu Asn
         355                 360                 365

Pro Arg Ile Gly Ser Phe Asp Leu Lys Tyr Phe Cys Glu Leu Arg Pro
     370                 375                 380

Gly Leu Ile Gly Trp Val Val Ile Asn Leu Ala Met Leu Leu Ala Glu
385                 390                 395                 400

Met Lys Ile His Asn Gln Ser Met Pro Ser Leu Ser Met Ile Leu Val
                 405                 410                 415

Asn Ser Phe Gln Leu Leu Tyr Val Val Asp Ala Leu Trp Asn Glu Glu
             420                 425                 430

Ala Val Leu Thr Thr Met Asp Ile Thr His Asp Gly Phe Gly Phe Met
         435                 440                 445

-continued

```
Leu Ala Phe Gly Asp Leu Val Trp Val Pro Phe Val Tyr Ser Leu Gln
    450                 455                 460

Ala Phe Tyr Leu Val Gly His Pro Ile Ala Ile Ser Trp Pro Val Ala
465                 470                 475                 480

Ala Ala Ile Thr Ile Leu Asn Cys Ile Gly Tyr Tyr Ile Phe Arg Ser
                485                 490                 495

Ala Asn Ser Gln Lys Asn Asn Phe Arg Arg Asn Pro Ala Asp Pro Lys
                500                 505                 510

Leu Ser Tyr Leu Lys Val Ile Pro Thr Ala Thr Gly Lys Gly Leu Leu
            515                 520                 525

Val Thr Gly Trp Trp Gly Phe Val Arg His Pro Asn Tyr Leu Gly Asp
        530                 535                 540

Ile Ile Met Ala Leu Ala Trp Ser Leu Pro Cys Gly Phe Asn His Ile
545                 550                 555                 560

Leu Pro Tyr Phe Tyr Val Ile Tyr Phe Ile Cys Leu Leu Val His Arg
                565                 570                 575

Glu Ala Arg Asp Glu His His Cys Lys Lys Tyr Gly Leu Ala Trp
                580                 585                 590

Glu Arg Tyr Cys Gln Arg Val Pro Tyr Thr His Ile Ser Leu His Leu
        595                 600                 605

Leu Glu His Ser Thr Tyr Leu Ile Cys Lys Leu Lys Tyr Thr Ser His
    610                 615                 620

Leu Cys Thr Trp Ser Val Cys Tyr Leu Gly Phe Lys His
625                 630                 635

<210> SEQ ID NO 9
<211> LENGTH: 615
<212> TYPE: PRT
<213> ORGANISM: Homo sapiens

<400> SEQUENCE: 9

Met Pro Ser Arg Lys Phe Ala Asp Gly Glu Val Val Arg Gly Arg Trp
1               5                   10                  15

Pro Gly Ser Ser Leu Tyr Tyr Glu Val Glu Ile Leu Ser His Asp Ser
                20                  25                  30

Thr Ser Gln Leu Tyr Thr Val Lys Tyr Lys Asp Gly Thr Glu Leu Glu
            35                  40                  45

Leu Lys Glu Asn Asp Ile Lys Pro Leu Thr Ser Phe Arg Gln Arg Lys
        50                  55                  60

Gly Gly Ser Thr Ser Ser Pro Ser Arg Arg Gly Ser Arg Ser
65                  70                  75                  80

Arg Ser Arg Ser Arg Ser Pro Gly Arg Pro Lys Ser Ala Arg Arg
                85                  90                  95

Ser Ala Ser Ala Ser His Gln Ala Asp Ile Lys Glu Ala Arg Arg Glu
                100                 105                 110

Val Glu Val Lys Leu Thr Pro Leu Ile Leu Lys Pro Phe Gly Asn Ser
            115                 120                 125

Ile Ser Arg Tyr Asn Gly Glu Pro Glu His Ile Glu Arg Asn Asp Ala
        130                 135                 140

Pro His Lys Asn Thr Gln Glu Lys Phe Ser Leu Ser Gln Glu Ser Ser
145                 150                 155                 160

Tyr Ile Ala Thr Gln Tyr Ser Leu Arg Pro Arg Arg Glu Glu Val Lys
                165                 170                 175

Leu Lys Glu Ile Asp Ser Lys Glu Glu Lys Tyr Val Ala Lys Glu Leu
```

-continued

```
                180                 185                 190
Ala Val Arg Thr Phe Glu Val Thr Pro Ile Arg Ala Lys Asp Leu Glu
            195                 200                 205
Phe Gly Gly Val Pro Gly Val Phe Leu Ile Met Phe Gly Leu Pro Val
210                 215                 220
Phe Leu Phe Leu Leu Leu Leu Met Cys Lys Gln Lys Asp Pro Ser Leu
225                 230                 235                 240
Leu Asn Phe Pro Pro Pro Leu Pro Ala Leu Tyr Glu Leu Trp Glu Thr
                245                 250                 255
Arg Val Phe Gly Val Tyr Leu Leu Trp Phe Leu Ile Gln Val Leu Phe
            260                 265                 270
Tyr Leu Leu Pro Ile Gly Lys Val Val Glu Gly Thr Pro Leu Ile Asp
        275                 280                 285
Gly Arg Arg Leu Lys Tyr Arg Leu Asn Gly Phe Tyr Pro Phe Ile Leu
290                 295                 300
Thr Ser Ala Val Ile Gly Thr Ser Leu Phe Gln Gly Val Glu Phe His
305                 310                 315                 320
Tyr Val Tyr Ser His Phe Leu Gln Phe Ala Leu Ala Ala Thr Val Phe
                325                 330                 335
Cys Val Val Leu Ser Val Tyr Leu Tyr Met Arg Ser Leu Lys Ala Pro
            340                 345                 350
Arg Asn Asp Leu Ser Pro Ala Ser Ser Gly Asn Ala Val Tyr Asp Phe
        355                 360                 365
Phe Ile Gly Arg Glu Leu Asn Pro Arg Ile Gly Thr Phe Asp Leu Lys
370                 375                 380
Tyr Phe Cys Glu Leu Arg Pro Gly Leu Ile Gly Trp Val Val Ile Asn
385                 390                 395                 400
Leu Val Met Leu Leu Ala Glu Met Lys Ile Gln Asp Arg Ala Val Pro
                405                 410                 415
Ser Leu Ala Met Ile Leu Val Asn Ser Phe Gln Leu Leu Tyr Val Val
            420                 425                 430
Asp Ala Leu Trp Asn Glu Glu Ala Leu Leu Thr Thr Met Asp Ile Ile
        435                 440                 445
His Asp Gly Phe Gly Phe Met Leu Ala Phe Gly Asp Leu Val Trp Val
450                 455                 460
Pro Phe Ile Tyr Ser Phe Gln Ala Phe Tyr Leu Val Ser His Pro Asn
465                 470                 475                 480
Glu Val Ser Trp Pro Met Ala Ser Leu Ile Ile Val Leu Lys Leu Cys
                485                 490                 495
Gly Tyr Val Ile Phe Arg Gly Ala Asn Ser Gln Lys Asn Ala Phe Arg
            500                 505                 510
Lys Asn Pro Ser Asp Pro Lys Leu Ala His Leu Lys Thr Ile His Thr
        515                 520                 525
Ser Ser Gly Lys Asn Leu Leu Val Ser Gly Trp Trp Gly Phe Val Arg
530                 535                 540
His Pro Asn Tyr Leu Gly Asp Leu Ile Met Ala Leu Ala Trp Ser Leu
545                 550                 555                 560
Pro Cys Gly Phe Asn His Ile Leu Pro Tyr Phe Tyr Ile Ile Tyr Phe
                565                 570                 575
Thr Met Leu Leu Val His Arg Glu Ala Arg Asp Glu Tyr His Cys Lys
            580                 585                 590
Lys Lys Tyr Gly Val Ala Trp Glu Lys Tyr Cys Gln Arg Val Pro Tyr
        595                 600                 605
```

Arg Ile Phe Pro Tyr Ile Tyr
    610             615

<210> SEQ ID NO 10
<211> LENGTH: 2975
<212> TYPE: DNA
<213> ORGANISM: Arabidopsis thaliana
<220> FEATURE:
<221> NAME/KEY: variation
<222> LOCATION: (1)...(2975)
<223> OTHER INFORMATION: N can be any nucleotide.

<400> SEQUENCE: 10

| | | | | |
|---|---|---|---|---|
| ctgaaattaa | acaaagcgag | aaaaggcgat | acaaacgatt | tcgaatgctt | catcttctcc | 60 |
| tttgaaaatc | cttcttctgc | ttaatgctgc | tagatatgga | tctcggtgtt | cttcttccat | 120 |
| cattgcaatc | tgtgagctgt | ctctttagct | tttgactgtt | gcaattgtta | ttgtgaaatt | 180 |
| tttgttcgct | tttggatcag | cttttgttaa | attcgttccg | agattttagg | tttatgtgct | 240 |
| ggtgttttac | ttcgtttact | tgggncgntg | gcggagaaat | tctccccggg | aaagttattc | 300 |
| gcggcgtcct | tttatcagat | ggctctcaac | ttcgttaccg | atgcaatggt | atatttgatt | 360 |
| tgatttactc | tctctacaat | tcctgagagt | ctgtgagctc | gaaagttcat | ttccattagt | 420 |
| ttggttaatt | caatttcagg | tctattggca | ctaatattgt | tggtagctat | ttngggaatc | 480 |
| tgtgcaaaac | ttggcattgt | atcacctctt | gtaagtgtag | ttacaagatt | tcgattgtat | 540 |
| ttctatgaat | ccgaatgcta | tatgctatat | gaatccgatt | gcaattgctt | tctcacactc | 600 |
| attccactga | gatgtttggt | aggtggttgc | ggatagagga | cttgagttac | tctcagctac | 660 |
| ttnnatttct | tgtgtttggg | gaagatgatc | aatccttagt | ccggngtctt | ggattttagn | 720 |
| tgngttacca | tcagattngc | tttgggtggt | gtgatttgta | atctccatga | tatctcttaa | 780 |
| tattctcagg | tgacattagc | attgtatgtt | actgggcgaa | gttcctcgaa | taagggttct | 840 |
| tccctaaagc | ctcatgtctc | aggaaatctt | gtacatgact | ggtactaaca | taatacaatt | 900 |
| gtagatctga | tactttcttg | ttacacaaaa | tgttgttaaa | agttatatat | tttgactcct | 960 |
| gcaagagcaa | aactaagaaa | taatctggta | ctatatagag | tttgaaacac | tgaattggac | 1020 |
| aagatgattc | tatagaactt | cgtagagtgt | tgagtaattt | ctcctagaac | ggttgtagct | 1080 |
| tcctcttttt | tcctttaac | cgcagtgact | ttagcttttg | gaacttttct | actgaaacta | 1140 |
| gaagttctgg | ttttgtcttt | cacttatctc | ttccaaacaa | ctgcttcaat | tttttctcat | 1200 |
| attgtttgtt | tcatgtgata | ggtggtttgg | aatacagctg | aatcctcagt | ttatgagcat | 1260 |
| tgatctcaag | taatccattt | ttctgttttt | tcttctattt | gtcagccaag | gctacatcat | 1320 |
| tgcttcagtt | tgttccgtac | tcaatcgagt | ggcagtttaa | taatgtaatc | agcagttatg | 1380 |
| catggttatg | atgaatggga | gttattcctt | gtgtaggttt | ttctttgtca | gagccgggat | 1440 |
| gatgggatgg | ctgcttatca | atctctctat | tctggcaaaa | agtgtgcagg | atggttcctt | 1500 |
| gagtcagtcg | atgatctta | ccagatcttc | tgtgcggtaa | atttggtttt | tacttacaaa | 1560 |
| tcttgcttct | tgaantctga | tcatctgtgt | tttgttagtt | ttgattagtt | ttataattgc | 1620 |
| agttatatat | attggatact | ttgttcatga | agaatacatg | acctctacgt | aagttcatgg | 1680 |
| cgtgttaagg | aaacacattt | gtcttaccaa | aaaatgacca | tttgcattat | tacatctact | 1740 |
| ttgattttac | tcttttcagg | tgggacataa | ttgcagagag | actaggcttc | atgctagtgt | 1800 |
| ttggagatct | cctgtggatt | cctttcactt | ttagcattca | ggcatgtaac | tgtgagcctg | 1860 |
| aacacaaaca | agatattaat | ttatcttatt | gacagtatct | tcttggcatg | ttacagttat | 1920 |

-continued

```
tctcggaaac aatattgttc tagaatgctt gatcactctg tgactgaatt gtcttctctc    1980
tggtacaggg ctggtggctt ttgcacaaca aagtagaact aacaattcct gcgattgtag    2040
tcaattgcct tgtcttcttg atagggtaag ttctgagaca tggggttatt ttccattctt    2100
acatatctac actaagaaac ccactatttc ttctttggca ggtacatggt ttttcgagga    2160
gctaacaaac aaaaacatat ctttaagaag aacccaaaaa caccaatatg gggcaagcct    2220
ccagtggtag ttggtggaaa gttactggtt tcaggctatt ggtatgttat atttatcttc    2280
tcttgtttct ttgcttggtt tcgccatctc tgtgtttgat tgttcatcat gctgggaata    2340
aagagttgaa agttccgcaa tgacacattt ccgataactt aggtgctgtt ttgtatatat    2400
gacaggggaa ttgcaaggca ctgtaattac cttggcgact tgatgcttgc tctgtccttc    2460
agtttgccat gtggaataag gtactcctnc tgcttgagtt cacttacagc taccaaaatc    2520
atgtagaaac taataccaat atcnaaacgt tcgaagttga tttggctgac ttaaagatat    2580
tgatctctaa ccatcatttg aaaagtctaa agctttcaag ttcatttccc aaagctgttt    2640
ttatgatatt tcgtctngtg tattctcagt tctccggttc catatttcta cccgatatac    2700
ctgctgatac tattgatatg gagagaacga agagacgaag ttcgatgtgc agagaagtac    2760
naggagatat gggcagagta tcttagactt gtccctgga gaatacttcc ttatgtttat    2820
tagatgtgcc aagagccaat tcatgaatcc tttcagattc atcctcttgt gtcttatttt    2880
ttcattaaat gtgacntgaa atgatcccat tatngcctnt tatcaatgct tgattgaaac    2940
tttgtagtac acgtttgaga attacttcag tcctt                              2975

<210> SEQ ID NO 11
<211> LENGTH: 131
<212> TYPE: DNA
<213> ORGANISM: Arabidopsis thaliana

<400> SEQUENCE: 11
ctgaaattaa acaaagcgag aaaaggcgat acaaacgatt tcgaatgctt catcttctcc     60
tttgaaaatc cttcttctgc ttaatgctgc tagatatgga tctcggtgtt cttcttccat    120
cattgcaatc t                                                         131

<210> SEQ ID NO 12
<211> LENGTH: 117
<212> TYPE: DNA
<213> ORGANISM: Arabidopsis thaliana

<400> SEQUENCE: 12
gtttatgtgc tggtgttta cttcgtttac ttggccgttg ccggagaaat tctccccggg     60
aaagttattc gcggcgtcct tttatcagat ggctctcaac ttcgttaccg atgcaat      117

<210> SEQ ID NO 13
<211> LENGTH: 72
<212> TYPE: DNA
<213> ORGANISM: Arabidopsis thaliana

<400> SEQUENCE: 13
ggtctattgg cactaatatt gttggtagct attttgggaa tctgtgcaaa acttggcatt     60
gtatcacctc tt                                                        72

<210> SEQ ID NO 14
<211> LENGTH: 55
<212> TYPE: DNA
```

<213> ORGANISM: Arabidopsis thaliana

<400> SEQUENCE: 14
gtggttgcgg atagaggact tgagttactc tcagctactt ttattttctg tgttt    55

<210> SEQ ID NO 15
<211> LENGTH: 93
<212> TYPE: DNA
<213> ORGANISM: Arabidopsis thaliana

<400> SEQUENCE: 15
tggtgacatt agcattgtat gttactgggc gaagttcctc gaataagggt tcttccctaa    60
agcctcatgt ctcaggaaat cttgtacatg act    93

<210> SEQ ID NO 16
<211> LENGTH: 49
<212> TYPE: DNA
<213> ORGANISM: Arabidopsis thaliana

<400> SEQUENCE: 16
ggtggtttgg aatacagctg aatcctcagt ttatgagcat tgatctcaa    49

<210> SEQ ID NO 17
<211> LENGTH: 120
<212> TYPE: DNA
<213> ORGANISM: Arabidopsis thaliana

<400> SEQUENCE: 17
gtttttcttt gtcagagccg ggatgatggg atggctgctt atcaatctct ctattctggc    60
aaaaagtgtg caggatggtt ccttgagtca gtcgatgatt ctttaccaga tcttctgtgc    120

<210> SEQ ID NO 18
<211> LENGTH: 48
<212> TYPE: DNA
<213> ORGANISM: Arabidopsis thaliana

<400> SEQUENCE: 18
gttatatata ttggactact ttgttcatga agaatacatg acctctac    48

<210> SEQ ID NO 19
<211> LENGTH: 79
<212> TYPE: DNA
<213> ORGANISM: Arabidopsis thaliana

<400> SEQUENCE: 19
gtgggacata attgcagaga gactaggctt catgctagtg tttggagatc tcctgtggat    60
tcctttcact tttagcatt    79

<210> SEQ ID NO 20
<211> LENGTH: 79
<212> TYPE: DNA
<213> ORGANISM: Arabidopsis thaliana

<400> SEQUENCE: 20
cagggctggt ggcttttgca caacaaagta gaactaacag ttcctgcgat tgtagtcaat    60
tgccttgtct tcttgatag    79

<210> SEQ ID NO 21
<211> LENGTH: 120
<212> TYPE: DNA
<213> ORGANISM: Arabidopsis thaliana

<400> SEQUENCE: 21
ggtacatggt ttttcgagga gctaacaaac aaaaacatat ctttaagaag aacccaaaaa        60
caccaatatg gggcaagcct ccagtggtag ttggtggaaa gttactggtt tcaggctatt       120

<210> SEQ ID NO 22
<211> LENGTH: 74
<212> TYPE: DNA
<213> ORGANISM: Arabidopsis thaliana

<400> SEQUENCE: 22
ggggaattgc aaggcactgt aattaccttg gcgacttgat gcttgctctg tccttcagtt        60
tgccatgtgg aata                                                          74

<210> SEQ ID NO 23
<211> LENGTH: 221
<212> TYPE: DNA
<213> ORGANISM: Arabidopsis thaliana

<400> SEQUENCE: 23
agttctccgg ttccatattt ctacccgata taccttctga tactattgat atggagagaa        60
cgaagagacg aggttcgatg tgcagagaag tacaaggaga tatgggcaga gtatcttaga       120
cttgtcccct ggagaatact tccttatgtt tattagatgt gccaagagcc aagtcatgaa       180
tcctttcaga ttcacctctt gttgtcttat tttttccata a                           221

<210> SEQ ID NO 24
<211> LENGTH: 70
<212> TYPE: DNA
<213> ORGANISM: Arabidopsis thaliana

<400> SEQUENCE: 24
tcttgtttta ttttagcaat gctcgaattg aaactttgta gtacactttt gaaaaataac        60
ttcagtcctt                                                               70